United States Patent
Knopf et al.

(10) Patent No.: US 7,612,040 B2
(45) Date of Patent: Nov. 3, 2009

(54) LEFTY POLYPEPTIDES AND DERIVATIVES THEREOF

(75) Inventors: John Knopf, Carlisle, MA (US); Jasbir Seehra, Lexington, MA (US); Ravindra Kumar, Shrewsbury, MA (US)

(73) Assignee: Acceleron Pharma Inc., Cambridge, MA (US)

( * ) Notice: Subject to any disclaimer, the term of this patent is extended or adjusted under 35 U.S.C. 154(b) by 33 days.

(21) Appl. No.: 11/479,181

(22) Filed: Jun. 30, 2006

(65) Prior Publication Data

US 2007/0042958 A1 Feb. 22, 2007

Related U.S. Application Data

(60) Provisional application No. 60/696,226, filed on Jul. 1, 2005.

(51) Int. Cl.
*A61K 38/16* (2006.01)
*A61K 38/18* (2006.01)
*A61K 38/19* (2006.01)
*C07K 14/00* (2006.01)
*C07K 14/475* (2006.01)
*C07K 14/51* (2006.01)

(52) U.S. Cl. .............................. 514/12; 514/2; 530/350

(58) Field of Classification Search ....................... None
See application file for complete search history.

(56) References Cited

U.S. PATENT DOCUMENTS 5,916,751 A 6/1999 Tabibzadeh et al.
6,027,917 A * 2/2000 Celeste et al. .............. 435/69.1
6,294,662 B1 9/2001 Tabibzadeh
6,428,966 B1 8/2002 Lee et al.
6,440,694 B1 * 8/2002 Bienkowski et al. ....... 435/69.1
6,492,493 B2 12/2002 Murray et al.
6,635,480 B1 10/2003 Lee et al.
6,649,588 B1 11/2003 Tabibzadeh et al.
6,673,341 B2 * 1/2004 Sukhatme ................ 424/130.1
6,683,156 B1 1/2004 Tabibzadeh
6,747,004 B1 6/2004 Tabibzadeh
7,355,018 B2 * 4/2008 Glass ........................ 530/399
2002/0086351 A1 * 7/2002 Ebner et al. ................ 435/69.1
2003/0022841 A1 1/2003 Lee et al.
2003/0032047 A1 2/2003 Tabibzadeh
2003/0149241 A1 8/2003 Celeste et al.
2004/0081647 A1 * 4/2004 Afeyan et al. ............ 424/94.63

(Continued)

FOREIGN PATENT DOCUMENTS

WO WO-02/12336 2/2002

OTHER PUBLICATIONS

Wells, 1990, Biochemistry 29:8509-8517.*

(Continued)

*Primary Examiner*—Elizabeth C. Kemmerer
(74) *Attorney, Agent, or Firm*—Ropes & Gray LLP

(57) ABSTRACT

The disclosure relates to Lefty derivatives and the uses of Lefty polypeptides as antagonists of the function of certain ligands such as Nodal, GDF-8 (Myostatin), and GDF-11. These derivatives may be fused to other functional heterologous proteins such as IgG, especially the Fc portion of IgG. According to the disclosure, Lefty polypeptides are useful in the treatment of a variety of disorders, including, for example, neuronal diseases, muscle and bone conditions, and metabolic disorders.

33 Claims, 7 Drawing Sheets

U.S. PATENT DOCUMENTS

2004/0146891 A1    7/2004  Lee et al.

OTHER PUBLICATIONS

Ngo et al., 1994, The Protein Folding Problem and Tertiary Structure Prediction, Merz et al., eds., Birkhauser, Boston, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Branford et al., "Nodal Signaling: Cryptic Lefty Mechanism of Antagonism Decoded", Current Biology, 14:R341-R343 (1994).
Chen et al., "The Vg1-related protein Gdf3 acts in a Nodal signaling pathway in the pre-gastrulation mouse embryo", Development, 133:319-329 (2005).
Chen et al., "Two Modes by which Lefty Proteins Inhibit Nodal Signaling", Current Biology, 14:618-624 (2004).
Cheng et al., "Lefty Blocks a subset of TGFβ Signals by Antagonizing EGF-CFC Coreceptors", PLoS Biology, 2:2:0215-0226 (2004).
Kosaki et al., "Characterization and mutation analysis of human *LEFTY A* and *LEFTY B*, homologues of murine genes implicated in left-right axis development," Am. J. Hum. Genet. 64:712-721 (1999).
Kothapalli et al., "Detection of ebaf, a Novel Human Gene of the Transforming Growth Factor β Superfamily", The American Society for Clinical Investigation, Inc., 99:2342-2350 (1997).
Lapraz et al., "RTK and TGF-β signaling pathways genes in the sa urchin genome," Developmental Biology, 300:132-152 (2006).
Mason et al., "Lefty Contributes to the Remodeling of Extracellular Matrix by Inhibition of Connective Tissue Growth Factor and Collagen mRNA Expression and Increased Proteolytic Activity in a Fibrosarcoma Model", The Journal of Biological Chemistry, 277:407-415 (2002).
Meno et al., "Diffusion of Nodal Signaling Activity in the Absense of the Feedback Inhibitor Lefty2", Developmental Cell, 1:127-138 (2001).
Oulad-Abdelghani et al., "lefty, a retinoic acid-inducible novel member of the transforming growth factorβ superfamily", Int. J. Dev. Biol., 42:23-32 (1998).
Rankin et al., "Regulation of left-right patterning in mice by growth/differentiation factor-1", Nature Genetics, 24:262-265 (2000).
Saijoh et al., "Distinct transcriptional regulatory mechanisms underlie left-right asymmetric expression of lefty-1 and lefty-2", Genes & Development, 13:259-269 (1999).
Sakuma et al., "Inhibition of Nodal signalling by Lefty mediated through interaction with common receptors and efficient diffusion", Genes to Cells, 7:401-412 (2002).
Tabibzadeh et al., "Lefty at the crossroad of 'stemness' and differentiative events", Stem Cells, www.StemCells.com, DOI: 10.1634/stemcells, (2006).
Ulloa et al., "Lefty Inhibits Receptor-regulated Smad Phosphorylation Induced by the Activated Transforming Growth Factor-β Receptor", The Journal of Biological Chemistry, 276:21397-21404 (2001).

* cited by examiner

Figure 3

Human Lefty-A protein (NCBI RefSeq ID NP_003231):

```
  1 MWPLWLCWAL WVLPLAGPGA ALTEEQLLGS LLRQLQLSEV PVLDRADMEK LVIPAHVRAQ
 61 YVVLLRRSHG DRSRGKRFSQ SFREVAGRFL ASEASTHLLV FGMEQRLPPN SELVQAVLRL
121 FQEPVPKAAL HRHGRLSPRS AQARVTVEWL RVRDDGSNRT SLIDSRLVSV HESGWKAFDV
181 TEAVNFWQQL SRPRQPLLLQ VSVQREHLGP LASGAHKLVR FASQGAPAGL GEPQLELHTL
241 DLRDYGAQGD CDPEAPMTEG TRCCRQEMYI DLQGMKWAKN WVLEPPGFLA YECVGTCQQP
301 PEALAFNWPF LGPRQCIASE TASLPMIVSI KEGGRTRPQV VSLPNMRVQK CSCASDGALV
361 PRRLQP
```

Human Lefty-B protein (NCBI RefSeq ID NP_066277):

```
  1 MQPLWLCWAL WVLPLASPGA ALTGEQLLGS LLRQLQLKEV PTLDRADMEE LVIPTHVRAQ
 61 YVALLQRSHG DRSRGKRFSQ SFREVAGRFL ALEASTHLLV FGMEQRLPPN SELVQAVLRL
121 FQEPVPKAAL HRHGRLSPRS ARARVTVEWL RVRDDGSNRT SLIDSRLVSV HESGWKAFDV
181 TEAVNFWQQL SRPRQPLLLQ VSVQREHLGP LASGAHKLVR FASQGAPAGL GEPQLELHTL
241 DLGDYGAQGD CDPEAPMTEG TRCCRQEMYI DLQGMKWAEN WVLEPPGFLA YECVGTCRQP
301 PEALAFKWPF LGPRQCIASE TDSLPMIVSI KEGGRTRPQV VSLPNMRVQK CSCASDGALV
361 PRRLQP
```

Figure 4

Human Lefty-A protein (34 kDa mature form):

```
  1  FSQSFREVAG RFLASEASTH LLVFGMEQRL PPNSELVQAV LRLFQEPVPK AALHRHGRLS
                                  (REGION 1)
 61  PRSAQARVTV EWLRVRDDGS NRTSLIDSRL VSVHESGWKA FDVTEAVNFW QQLSRPRQPL
                               (REGION 1, CONT.)
121  LLQVSVQREH LGPLASGAHK LVRFASQGAP AGLGEPQLEL HTLDLRDYGA QGDCDPEAPM
                               (REGION 1, CONT.)
181  TEGTRCCRQE MYIDLQGMKW AKNWVLEPPG FLAYECVGTC QQPPEALAFN WPFLGPRQCI
            (REGION 2)                                (REGION 3)
241  ASETASLPMI VSIKEGGRTR PQVVSLPNMR VQKCSCASDG ALVPRRLQP
            (REGION 4)                      (REGION 5)
```

Human Lefty-B protein (34 kDa mature form):

```
  1  FSQSFREVAG RFLALEAST HLLVFGMEQR LPPNSELVQA VLRLFQEPVPK AALHRHGRLS
                                  (REGION 1)
 61  PRSARARVTV EWLRVRDDG SNRTSLIDSR LVSVHESGWK AFDVTEAVNFW QQLSRPRQPL
                               (REGION 1, CONT.)
121  LLQVSVQREH LGPLASGAH KLVRFASQGA PAGLGEPQLE LHTLDLGDYGA QGDCDPEAPM
                               (REGION 1, CONT.)
181  TEGTRCCRQE MYIDLQGMK WAENWVLEPP GFLAYECVGT CRQPPEALAFK WPFLGPRQCI
            (REGION 2)                                (REGION 3)
241  ASETDSLPMI VSIKEGGRT RPQVVSLPNM RVQKCSCASD GALVPRRLQP
            (REGION 4)                      (REGION 5)
```

Figure 5

SEQUENCE LISTING

<160> NUMBER OF SEQ ID NOS: 28

<210> SEQ ID NO 1
<211> LENGTH: 366
<212> TYPE: PRT
<213> ORGANISM: Homo sapiens

<400> SEQUENCE: 1

```
Met Trp Pro Leu Trp Leu Cys Trp Ala Leu Trp Val Leu Pro Leu Ala
 1               5                  10                  15

Gly Pro Gly Ala Ala Leu Thr Glu Glu Gln Leu Leu Gly Ser Leu Leu
            20                  25                  30

Arg Gln Leu Gln Leu Ser Glu Val Pro Val Leu Asp Arg Ala Asp Met
        35                  40                  45

Glu Lys Leu Val Ile Pro Ala His Val Arg Ala Gln Tyr Val Val Leu
    50                  55                  60

Leu Arg Arg Ser His Gly Asp Arg Ser Arg Gly Lys Arg Phe Ser Gln
65                  70                  75                  80

Ser Phe Arg Glu Val Ala Gly Arg Phe Leu Ala Ser Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Gln Ala Arg
    130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
    210                 215                 220
```

```
Gly Ala Pro Ala Gly Leu Gly Glu Pro Gln Leu Glu Leu His Thr Leu
225                 230                 235                 240

Asp Leu Arg Asp Tyr Gly Ala Gln Gly Asp Cys Asp Pro Glu Ala Pro
            245                 250                 255

Met Thr Glu Gly Thr Arg Cys Cys Arg Gln Glu Met Tyr Ile Asp Leu
        260                 265                 270

Gln Gly Met Lys Trp Ala Lys Asn Trp Val Leu Glu Pro Pro Gly Phe
    275                 280                 285

Leu Ala Tyr Glu Cys Val Gly Thr Cys Gln Gln Pro Pro Glu Ala Leu
290                 295                 300

Ala Phe Asn Trp Pro Phe Leu Gly Pro Arg Gln Cys Ile Ala Ser Glu
305                 310                 315                 320

Thr Ala Ser Leu Pro Met Ile Val Ser Ile Lys Glu Gly Gly Arg Thr
            325                 330                 335

Arg Pro Gln Val Val Ser Leu Pro Asn Met Arg Val Gln Lys Cys Ser
        340                 345                 350

Cys Ala Ser Asp Gly Ala Leu Val Pro Arg Arg Leu Gln Pro
    355                 360                 365
```

<210> SEQ ID NO 2
<211> LENGTH: 366
<212> TYPE: PRT
<213> ORGANISM: Homo sapiens

<400> SEQUENCE: 2

```
Met Gln Pro Leu Trp Leu Cys Trp Ala Leu Trp Val Leu Pro Leu Ala
1               5                   10                  15

Ser Pro Gly Ala Ala Leu Thr Gly Glu Gln Leu Leu Gly Ser Leu Leu
            20                  25                  30

Arg Gln Leu Gln Leu Lys Glu Val Pro Thr Leu Asp Arg Ala Asp Met
        35                  40                  45

Glu Glu Leu Val Ile Pro Thr His Val Arg Ala Gln Tyr Val Ala Leu
50                  55                  60

Leu Gln Arg Ser His Gly Asp Arg Ser Arg Gly Lys Arg Phe Ser Gln
65                  70                  75                  80

Ser Phe Arg Glu Val Ala Gly Arg Phe Leu Ala Leu Glu Ala Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Lys Ala
        115                 120                 125

Ala Leu His Arg His Gly Arg Leu Ser Pro Arg Ser Ala Arg Ala Arg
130                 135                 140

Val Thr Val Glu Trp Leu Arg Val Arg Asp Asp Gly Ser Asn Arg Thr
145                 150                 155                 160

Ser Leu Ile Asp Ser Arg Leu Val Ser Val His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Leu Ala Ser Gly Ala His Lys Leu Val Arg Phe Ala Ser Gln
210                 215                 220

Gly Ala Pro Ala Gly Leu Gly Glu Pro Gln Leu Glu Leu His Thr Leu
225                 230                 235                 240
```

```
Asp Leu Gly Asp Tyr Gly Ala Gln Gly Asp Cys Asp Pro Glu Ala Pro
                245                 250                 255

Met Thr Glu Gly Thr Arg Cys Cys Arg Gln Glu Met Tyr Ile Asp Leu
            260                 265                 270

Gln Gly Met Lys Trp Ala Glu Asn Trp Val Leu Glu Pro Pro Gly Phe
        275                 280                 285

Leu Ala Tyr Glu Cys Val Gly Thr Cys Arg Gln Pro Pro Glu Ala Leu
    290                 295                 300

Ala Phe Lys Trp Pro Phe Leu Gly Pro Arg Gln Cys Ile Ala Ser Glu
305                 310                 315                 320

Thr Asp Ser Leu Pro Met Ile Val Ser Ile Lys Glu Gly Gly Arg Thr
                325                 330                 335

Arg Pro Gln Val Val Ser Leu Pro Asn Met Arg Val Gln Lys Cys Ser
            340                 345                 350

Cys Ala Ser Asp Gly Ala Leu Val Pro Arg Arg Leu Gln Pro
        355                 360                 365

<210> SEQ ID NO 3
<211> LENGTH: 368
<212> TYPE: PRT
<213> ORGANISM: Mus musculus

<400> SEQUENCE: 3

Met Pro Phe Leu Trp Leu Cys Trp Ala Leu Trp Ala Leu Ser Leu Val
1               5                   10                  15

Ser Leu Arg Glu Ala Leu Thr Gly Glu Gln Ile Leu Gly Ser Leu Leu
            20                  25                  30

Gln Gln Leu Gln Leu Asp Gln Pro Pro Val Leu Asp Lys Ala Asp Val
        35                  40                  45

Glu Gly Met Val Ile Pro Ser His Val Arg Thr Gln Tyr Val Ala Leu
    50                  55                  60

Leu Gln His Ser His Ala Ser Arg Ser Arg Gly Lys Arg Phe Ser Gln
65                  70                  75                  80

Asn Leu Arg Glu Val Ala Gly Arg Phe Leu Val Ser Glu Thr Ser Thr
                85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Arg Thr
        115                 120                 125

Ala Leu Arg Arg Gln Lys Arg Leu Ser Pro His Ser Ala Arg Ala Arg
    130                 135                 140

Val Thr Ile Glu Trp Leu Arg Phe Arg Asp Asp Gly Ser Asn Arg Thr
145                 150                 155                 160

Ala Leu Ile Asp Ser Arg Leu Val Ser Ile His Glu Ser Gly Trp Lys
                165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
        195                 200                 205

Gly Pro Gly Thr Trp Ser Ser His Lys Leu Val Arg Phe Ala Ala Gln
    210                 215                 220

Gly Thr Pro Asp Gly Lys Gly Gln Gly Glu Pro Gln Leu Glu Leu His
225                 230                 235                 240

Thr Leu Asp Leu Lys Asp Tyr Gly Ala Gln Gly Asn Cys Asp Pro Glu
```

-continued

```
            245                 250                 255
Ala Pro Val Thr Glu Gly Thr Arg Cys Cys Arg Gln Glu Met Tyr Leu
            260                 265                 270

Asp Leu Gln Gly Met Lys Trp Ala Glu Asn Trp Ile Leu Glu Pro Pro
            275                 280                 285

Gly Phe Leu Thr Tyr Glu Cys Val Gly Ser Cys Leu Gln Leu Pro Glu
            290                 295                 300

Ser Leu Thr Ser Arg Trp Pro Phe Leu Gly Pro Arg Gln Cys Val Ala
305                 310                 315                 320

Ser Glu Met Thr Ser Leu Pro Met Ile Val Ser Val Lys Glu Gly Gly
            325                 330                 335

Arg Thr Arg Pro Gln Val Val Ser Leu Pro Asn Met Arg Val Gln Thr
            340                 345                 350

Cys Ser Cys Ala Ser Asp Gly Ala Leu Ile Pro Arg Arg Leu Gln Pro
            355                 360                 365

<210> SEQ ID NO 4
<211> LENGTH: 368
<212> TYPE: PRT
<213> ORGANISM: Mus musculus

<400> SEQUENCE: 4

Met Lys Ser Leu Trp Leu Cys Trp Ala Leu Trp Val Leu Pro Leu Ala
1               5                   10                  15

Gly Pro Gly Ala Ala Met Thr Glu Glu Gln Val Leu Ser Ser Leu Leu
            20                  25                  30

Gln Gln Leu Gln Leu Ser Gln Ala Pro Thr Leu Asp Ser Ala Asp Val
            35                  40                  45

Glu Glu Met Ala Ile Pro Thr His Val Arg Ser Gln Tyr Val Ala Leu
            50                  55                  60

Leu Gln Gly Ser His Ala Asp Arg Ser Arg Gly Lys Arg Phe Ser Gln
65                  70                  75                  80

Asn Phe Arg Glu Val Ala Gly Arg Phe Leu Met Ser Glu Thr Ser Thr
            85                  90                  95

His Leu Leu Val Phe Gly Met Glu Gln Arg Leu Pro Pro Asn Ser Glu
            100                 105                 110

Leu Val Gln Ala Val Leu Arg Leu Phe Gln Glu Pro Val Pro Arg Thr
            115                 120                 125

Ala Leu Arg Arg Phe Glu Arg Leu Ser Pro His Ser Ala Arg Ala Arg
            130                 135                 140

Val Thr Ile Glu Trp Leu Arg Val Arg Glu Asp Gly Ser Asn Arg Thr
145                 150                 155                 160

Ala Leu Ile Asp Ser Arg Leu Val Ser Ile His Glu Ser Gly Trp Lys
            165                 170                 175

Ala Phe Asp Val Thr Glu Ala Val Asn Phe Trp Gln Gln Leu Ser Arg
            180                 185                 190

Pro Arg Gln Pro Leu Leu Leu Gln Val Ser Val Gln Arg Glu His Leu
            195                 200                 205

Gly Pro Gly Thr Trp Ser Ala His Lys Leu Val Arg Phe Ala Ala Gln
            210                 215                 220

Gly Thr Pro Asp Gly Lys Gly Gln Gly Glu Pro Gln Leu Glu Leu His
225                 230                 235                 240

Thr Leu Asp Leu Lys Asp Tyr Gly Ala Gln Gly Asn Cys Asp Pro Glu
            245                 250                 255
```

```
Val Pro Val Thr Glu Gly Thr Arg Cys Cys Arg Gln Glu Met Tyr Leu
            260                 265                 270

Asp Leu Gln Gly Met Lys Trp Ala Glu Asn Trp Ile Leu Glu Pro Pro
            275                 280                 285

Gly Phe Leu Thr Tyr Glu Cys Val Gly Ser Cys Leu Gln Leu Pro Glu
            290                 295                 300

Ser Leu Thr Ile Gly Trp Pro Phe Leu Gly Pro Arg Gln Cys Val Ala
305                 310                 315                 320

Ser Glu Met Thr Ser Leu Pro Met Ile Val Ser Val Lys Glu Gly Gly
                325                 330                 335

Arg Thr Arg Pro Gln Val Val Ser Leu Pro Asn Met Arg Val Gln Thr
            340                 345                 350

Cys Ser Cys Ala Ser Asp Gly Ala Leu Ile Pro Arg Gly Ile Asp Leu
            355                 360                 365

<210> SEQ ID NO 5
<211> LENGTH: 33
<212> TYPE: PRT
<213> ORGANISM: Homo sapiens

<400> SEQUENCE: 5

Cys Arg Gln Glu Met Tyr Ile Asp Leu Gln Gly Met Lys Trp Ala Lys
1               5                   10                  15

Asn Trp Val Leu Glu Pro Pro Gly Phe Leu Ala Tyr Glu Cys Val Gly
                20                  25                  30

Thr

<210> SEQ ID NO 6
<211> LENGTH: 36
<212> TYPE: PRT
<213> ORGANISM: Homo sapiens

<400> SEQUENCE: 6

Cys Ile Ala Ser Glu Thr Ala Ser Leu Pro Met Ile Val Ser Ile Lys
1               5                   10                  15

Glu Gly Gly Arg Thr Arg Pro Gln Val Val Ser Leu Pro Asn Met Arg
                20                  25                  30

Val Gln Lys Cys
            35

<210> SEQ ID NO 7
<211> LENGTH: 33
<212> TYPE: PRT
<213> ORGANISM: Homo sapiens

<400> SEQUENCE: 7

Cys Arg Gln Glu Met Tyr Ile Asp Leu Gln Gly Met Lys Trp Ala Glu
1               5                   10                  15

Asn Trp Val Leu Glu Pro Pro Gly Phe Leu Ala Tyr Glu Cys Val Gly
                20                  25                  30

Thr

<210> SEQ ID NO 8
<211> LENGTH: 36
<212> TYPE: PRT
<213> ORGANISM: Homo sapiens

<400> SEQUENCE: 8

Cys Ile Ala Ser Glu Thr Asp Ser Leu Pro Met Ile Val Ser Ile Lys
```

-continued

```
              1               5                  10                 15
        Glu Gly Gly Arg Thr Arg Pro Gln Val Val Ser Leu Pro Asn Met Arg
                        20                 25                 30

Val Gln Lys Cys
                    35

<210> SEQ ID NO 9
<211> LENGTH: 289
<212> TYPE: PRT
<213> ORGANISM: Homo sapiens

<400> SEQUENCE: 9

Phe Ser Gln Ser Phe Arg Glu Val Ala Gly Arg Phe Leu Ala Ser Glu
         1               5                  10                 15

Ala Ser Thr His Leu Leu Val Phe Gly Met Glu Gln Arg Leu Pro Pro
                        20                 25                 30

Asn Ser Glu Leu Val Gln Ala Val Leu Arg Leu Phe Gln Glu Pro Val
                    35                 40                 45

Pro Lys Ala Ala Leu His Arg His Gly Arg Leu Ser Pro Arg Ser Ala
         50                 55                 60

Gln Ala Arg Val Thr Val Glu Trp Leu Arg Val Arg Asp Asp Gly Ser
         65                 70                 75                 80

Asn Arg Thr Ser Leu Ile Asp Ser Arg Leu Val Ser Val His Glu Ser
                        85                 90                 95

Gly Trp Lys Ala Phe Asp Val Thr Glu Ala Val Asn Phe Trp Gln Gln
                    100                105                110

Leu Ser Arg Pro Arg Gln Pro Leu Leu Leu Gln Val Ser Val Gln Arg
                    115                120                125

Glu His Leu Gly Pro Leu Ala Ser Gly Ala His Lys Leu Val Arg Phe
                    130                135                140

Ala Ser Gln Gly Ala Pro Ala Gly Leu Gly Glu Pro Gln Leu Glu Leu
        145                150                155                160

His Thr Leu Asp Leu Arg Asp Tyr Gly Ala Gln Gly Asp Cys Asp Pro
                        165                170                175

Glu Ala Pro Met Thr Glu Gly Thr Arg Cys Cys Arg Gln Glu Met Tyr
                    180                185                190

Ile Asp Leu Gln Gly Met Lys Trp Ala Lys Asn Trp Val Leu Glu Pro
                    195                200                205

Pro Gly Phe Leu Ala Tyr Glu Cys Val Gly Thr Cys Gln Gln Pro Pro
                    210                215                220

Glu Ala Leu Ala Phe Asn Trp Pro Phe Leu Gly Pro Arg Gln Cys Ile
        225                230                235                240

Ala Ser Glu Thr Ala Ser Leu Pro Met Ile Val Ser Ile Lys Glu Gly
                        245                250                255

Gly Arg Thr Arg Pro Gln Val Val Ser Leu Pro Asn Met Arg Val Gln
                    260                265                270

Lys Cys Ser Cys Ala Ser Asp Gly Ala Leu Val Pro Arg Arg Leu Gln
                    275                280                285

Pro

<210> SEQ ID NO 10
<211> LENGTH: 289
<212> TYPE: PRT
<213> ORGANISM: Homo sapiens

<400> SEQUENCE: 10
```

```
Phe Ser Gln Ser Phe Arg Glu Val Ala Gly Arg Phe Leu Ala Leu Glu
1               5                   10                  15

Ala Ser Thr His Leu Leu Val Phe Gly Met Glu Gln Arg Leu Pro Pro
            20                  25                  30

Asn Ser Glu Leu Val Gln Ala Val Leu Arg Leu Phe Gln Glu Pro Val
        35                  40                  45

Pro Lys Ala Ala Leu His Arg His Gly Arg Leu Ser Pro Arg Ser Ala
    50                  55                  60

Arg Ala Arg Val Thr Val Glu Trp Leu Arg Val Arg Asp Asp Gly Ser
65                  70                  75                  80

Asn Arg Thr Ser Leu Ile Asp Ser Arg Leu Val Ser Val His Glu Ser
                85                  90                  95

Gly Trp Lys Ala Phe Asp Val Thr Glu Ala Val Asn Phe Trp Gln Gln
            100                 105                 110

Leu Ser Arg Pro Arg Gln Pro Leu Leu Leu Gln Val Ser Val Gln Arg
        115                 120                 125

Glu His Leu Gly Pro Leu Ala Ser Gly Ala His Lys Leu Val Arg Phe
130                 135                 140

Ala Ser Gln Gly Ala Pro Ala Gly Leu Gly Glu Pro Gln Leu Glu Leu
145                 150                 155                 160

His Thr Leu Asp Leu Gly Asp Tyr Gly Ala Gln Gly Asp Cys Asp Pro
                165                 170                 175

Glu Ala Pro Met Thr Glu Gly Thr Arg Cys Cys Arg Gln Glu Met Tyr
            180                 185                 190

Ile Asp Leu Gln Gly Met Lys Trp Ala Glu Asn Trp Val Leu Glu Pro
        195                 200                 205

Pro Gly Phe Leu Ala Tyr Glu Cys Val Gly Thr Cys Arg Gln Pro Pro
    210                 215                 220

Glu Ala Leu Ala Phe Lys Trp Pro Phe Leu Gly Pro Arg Gln Cys Ile
225                 230                 235                 240

Ala Ser Glu Thr Asp Ser Leu Pro Met Ile Val Ser Ile Lys Glu Gly
                245                 250                 255

Gly Arg Thr Arg Pro Gln Val Val Ser Leu Pro Asn Met Arg Val Gln
            260                 265                 270

Lys Cys Ser Cys Ala Ser Asp Gly Ala Leu Val Pro Arg Arg Leu Gln
        275                 280                 285

Pro

<210> SEQ ID NO 11
<211> LENGTH: 345
<212> TYPE: PRT
<213> ORGANISM: Homo sapiens

<400> SEQUENCE: 11

Leu Thr Glu Glu Gln Leu Leu Gly Ser Leu Leu Arg Gln Leu Gln Leu
1               5                   10                  15

Ser Glu Val Pro Val Leu Asp Arg Ala Asp Met Glu Lys Leu Val Ile
            20                  25                  30

Pro Ala His Val Arg Ala Gln Tyr Val Val Leu Leu Arg Arg Ser His
        35                  40                  45

Gly Asp Arg Ser Arg Gly Lys Arg Phe Ser Gln Ser Phe Arg Glu Val
    50                  55                  60

Ala Gly Arg Phe Leu Ala Ser Glu Ala Ser Thr His Leu Leu Val Phe
65                  70                  75                  80
```

Gly Met Glu Gln Arg Leu Pro Pro Asn Ser Glu Leu Val Gln Ala Val
                85                  90                  95

Leu Arg Leu Phe Gln Glu Pro Val Pro Lys Ala Ala Leu His Gly His
            100                 105                 110

Gly Arg Leu Ser Pro Arg Ser Ala Gln Ala Arg Val Thr Val Glu Trp
        115                 120                 125

Leu Arg Val Arg Asp Asp Gly Ser Asn Arg Thr Ser Leu Ile Asp Ser
    130                 135                 140

Arg Leu Val Ser Val His Glu Ser Gly Trp Lys Ala Phe Asp Val Thr
145                 150                 155                 160

Glu Ala Val Asn Phe Trp Gln Gln Leu Ser Arg Pro Arg Gln Pro Leu
                165                 170                 175

Leu Leu Gln Val Ser Val Gln Arg Glu His Leu Gly Pro Leu Ala Ser
            180                 185                 190

Gly Ala His Lys Leu Val Arg Phe Ala Ser Gln Gly Ala Pro Ala Gly
        195                 200                 205

Leu Gly Glu Pro Gln Leu Glu Leu His Thr Leu Asp Leu Arg Asp Tyr
    210                 215                 220

Gly Ala Gln Gly Asp Cys Asp Pro Glu Ala Pro Met Thr Glu Gly Thr
225                 230                 235                 240

Arg Cys Cys Arg Gln Glu Met Tyr Ile Asp Leu Gln Gly Met Lys Trp
                245                 250                 255

Ala Lys Asn Trp Val Leu Glu Pro Pro Gly Phe Leu Ala Tyr Glu Cys
            260                 265                 270

Val Gly Thr Cys Gln Gln Pro Pro Glu Ala Leu Ala Phe Asn Trp Pro
        275                 280                 285

Phe Leu Gly Pro Arg Gln Cys Ile Ala Ser Glu Thr Ala Ser Leu Pro
    290                 295                 300

Met Ile Val Ser Ile Lys Glu Gly Gly Arg Thr Arg Pro Gln Val Val
305                 310                 315                 320

Ser Leu Pro Asn Met Arg Val Gln Lys Cys Ser Cys Ala Ser Asp Gly
                325                 330                 335

Ala Leu Val Pro Arg Arg Leu Gln Pro
            340                 345

<210> SEQ ID NO 12
<211> LENGTH: 231
<212> TYPE: PRT
<213> ORGANISM: Homo sapiens

<400> SEQUENCE: 12

Leu Ser Pro Arg Ser Ala Gln Ala Arg Val Thr Val Glu Trp Leu Arg
 1               5                  10                  15

Val Arg Asp Asp Gly Ser Asn Arg Thr Ser Leu Ile Asp Ser Arg Leu
            20                  25                  30

Val Ser Val His Glu Ser Gly Trp Lys Ala Phe Asp Val Thr Glu Ala
        35                  40                  45

Val Asn Phe Trp Gln Gln Leu Ser Arg Pro Arg Gln Pro Leu Leu Leu
    50                  55                  60

Gln Val Ser Val Gln Arg Glu His Leu Gly Pro Leu Ala Ser Gly Ala
65                  70                  75                  80

His Lys Leu Val Arg Phe Ala Ser Gln Gly Ala Pro Ala Gly Leu Gly
                85                  90                  95

Glu Pro Gln Leu Glu Leu His Thr Leu Asp Leu Arg Asp Tyr Gly Ala

-continued

```
              100                 105                 110
Gln Gly Asp Cys Asp Pro Glu Ala Pro Met Thr Glu Gly Thr Arg Cys
        115                 120                 125

Cys Arg Gln Glu Met Tyr Ile Asp Leu Gln Gly Met Lys Trp Ala Lys
    130                 135                 140

Asn Trp Val Leu Glu Pro Pro Gly Phe Leu Ala Tyr Glu Cys Val Gly
145                 150                 155                 160

Thr Cys Gln Gln Pro Pro Glu Ala Leu Ala Phe Asn Trp Pro Phe Leu
                165                 170                 175

Gly Pro Arg Gln Cys Ile Ala Ser Glu Thr Ala Ser Leu Pro Met Ile
            180                 185                 190

Val Ser Ile Lys Glu Gly Gly Arg Thr Arg Pro Gln Val Val Ser Leu
        195                 200                 205

Pro Asn Met Arg Val Gln Lys Cys Ser Cys Ala Ser Asp Gly Ala Leu
    210                 215                 220

Val Pro Arg Arg Leu Gln Pro
225                 230
```

<210> SEQ ID NO 13
<211> LENGTH: 1583
<212> TYPE: DNA
<213> ORGANISM: Mus musculus

<400> SEQUENCE: 13

| | | | | | |
|---|---|---|---|---|---|
| aggacacctc | agggacacac | acatccaagg | ctcctcttcc | cggacagcac | catgccattc | 60 |
| ctgtggctct | gctgggcact | ctgggcactg | tcgctggtta | gcctcaggga | agccctgacc | 120 |
| ggagagcaga | tcctgggcag | cctgctgcaa | cagctgcagc | tcgatcaacc | gccagtcctg | 180 |
| gacaaggctg | atgtggaagg | gatggtcatc | ccctcgcacg | tgaggactca | gtatgtggcc | 240 |
| ctgctacaac | acagccatgc | cagccgctcc | gaggcaagaa | ggttcagcca | gaaccttcga | 300 |
| gaggtggcag | gcaggttcct | ggtgtcagag | acctccactc | acctgctagt | gttcggaatg | 360 |
| gagcagcggc | tgccgcctaa | cagcgagctg | gtgcaggctg | tgctgcggct | gttccaggag | 420 |
| cctgtgccca | gaacagctct | ccggaggcaa | aagaggctgt | ccccacacag | tgcccgggct | 480 |
| cgggtcacca | ttgaatggct | gcgcttccgc | gacgacggct | ccaaccgcac | tgcccttatc | 540 |
| gattctaggc | tcgtgtccat | ccacgagagc | ggctggaagg | ccttcgacgt | gaccgaggcc | 600 |
| gtgaacttct | ggcagcagct | gagccggccg | aggcagccgc | tgctgctcca | ggtgtcggtg | 660 |
| cagagggagc | atctggggcc | gggaacctgg | agctcacaca | agttggttcg | tttcgcggcg | 720 |
| caggggacgc | cggatggcaa | ggggcagggc | gagccacagc | tggagctgca | cacgctggac | 780 |
| ctcaaggact | atggagctca | aggcaattgt | gaccccgagg | caccagtgac | tgaaggcacc | 840 |
| cgatgctgtc | gccaggagat | gtacctggac | ctgcagggga | tgaagtgggc | gagaactgg | 900 |
| atcctagaac | cgccagggtt | cctgacatat | gaatgtgtgg | gcagctgcct | gcagctaccg | 960 |
| gagtccctga | ccagcaggtg | gccatttctg | ggcctcggc | agtgtgtcgc | ctcagagatg | 1020 |
| acctccctgc | ccatgattgt | cagcgtgaag | gagggaggca | ggaccaggcc | tcaagtggtc | 1080 |
| agcctgccca | acatgagggt | gcagacctgt | agctgcgcct | cagatggggc | gctcataccc | 1140 |
| aggaggctgc | agccataggc | gcggggtgtg | gcttccccaa | ggatgtgcct | ttcatgcaaa | 1200 |
| tctgaagtgc | tcattatact | gggagagctg | gggattctaa | ctccctaatg | gcaatccct | 1260 |
| gtgtgtgctc | tttgcttcct | ctgaagtagc | ctcatccta | aattttttacc | ttcgaggaat | 1320 |
| gtgactcgct | ggcccctgga | ggcgctctga | cccagtggtc | tctgtccttc | atattgttca | 1380 |

```
ctgcactgta tgcgaagcac ttacatgtat agatactgca aaccaaggac agaatcccca    1440
attgccattg ttcccttaat ttgtcgctga atctgggctg agtcccagtc ttgactctgg    1500
acctaagcca caagttgggc aaacatgtcc aacctaggca atactggctt tgctagatgt    1560
gaataaaata tgctttgttt tgt                                           1583
```

<210> SEQ ID NO 14
<211> LENGTH: 2534
<212> TYPE: DNA
<213> ORGANISM: Mus musculus

<400> SEQUENCE: 14

```
gtcccaagaa cttttcaggg cactttagg gacgcatata tccacgattc ctcctgggca      60
gcgccatgaa gtccctgtgg ctttgctggg cactctgggt actgcccctg gctggccctg    120
gggcagcgat gaccgaggaa caggtcctga gcagtctact gcagcagctg cagctcagcc    180
aggcccccac cctggacagc gcggatgtgg aggagatggc catccctacc cacgtgaggt    240
cccagtatgt ggccctgctg cagggaagtc acgctgaccg ctcccgaggc aagaggttca    300
gccagaattt tcgagaggtg gcaggcaggt tcctgatgtc agagacctcc actcacctgc    360
tagtgttcgg aatggagcag cggctgccgc ctaacagcga gctggtgcag gctgtgctgc    420
ggctgttcca ggagcctgtg cccagaacag ctctccggag gtttgagagg ctgtccccac    480
acagtgcccg ggctcgggtc accattgaat ggctgagagt ccgtgaggat ggctccaatc    540
gcactgccct catcgactct aggctcgtgt ccatccacga gagcggctgg aaggccttcg    600
acgtgaccga ggccgtgaac ttctggcagc agctgagccg gccgaggcag ccgctgctgc    660
tccaggtgtc ggtgcagagg gagcatctgg ggccggggac ctggagcgca cacaagttgg    720
tccgtttcgc ggcgcagggg acgccggacg gcaaggggca gggcgagcca cagctggagc    780
tgcacacgct ggacctcaag gactacggag ctcaaggcaa ttgtgacccc gaggtaccag    840
tgactgaagg caccgatgc tgtcgccagg agatgtacct ggacctgcag gggatgaagt    900 gggcgagaa ctggatccta gaaccgccag ggttcctgac gtatgaatgt gtgggcagct    960
gcctgcagct accagagtcc ctgaccatcg ggtggccatt tctggggcct cggcagtgtg   1020
ttgcctcaga gatgaacctcc ttgccccatga ttgtcagtgt gaaggaggga ggcaggacca   1080
ggcctcaagt ggtcagcctg cccaacatga gggtgcagac ctgtagctgc gcctcagatg   1140
gggcgctcat acccagggggg atagatctgt agtctccctg tccacagatg tattctcagt   1200
gagcttgtcc taacttagtg ctctcgtcag acctttgctc tacagtcttg gttttcttgt   1260
ccatcaccca gtttaagcac ttacatgggt aaatcatgtc actccagtag gacacactga   1320
ccccacttag ccaaggacat ggctatgcag tgaacaggtt cgcatctgag tctgtttct    1380 ggccagaact cagcttaatg tacaacaaaa ccctacggtg agaacagggg aatcaaaagc   1440
tcgtttactc ttacaccgtg attactggca tcaacgtacc atgtcaggga ctgcccacag   1500
caggctggga gggagacatc tcagaagcct gcggcagctc cttgtgaaaa accgttgttc   1560
ccatttctcc taaccttagc cctagacaag agctgtatag atttcatgtg tgtgactgct   1620
tttcagttgg ccttggtgtt catagttatt ctatattatt tgactttcct actccttttct   1680 ccttctgccc tggtgaattc tatgaaacta gatgttcctt gatgtaatga ttcttaaaca   1740
attaaaaagt tgaggcatgg gacacagcac agcacagtcc tgatggccca ggtgcatgct   1800
gtagatgtat tctgtgtgct cttatcttgg aaacaatgca ataactttgc aatgttagtt   1860
```

```
cagattaatg tttgacttgc aaagaaagtt tgaagaaatt attagaaagt gaaatagagc      1920
caacactggg atcccgaaaa gaaaaaagct attgaagtta tgaaataagt tttgcacaaa      1980
atttgagagt gtttcctgga taagcaagta tagaatacat aaaatcttat attagtaaaa      2040
ctaagccaaa acaccgggac tcttaggagg gtcactgcgt gcaatgtgca gaagcagaaa      2100
gctggcagaa ctgccgagtt aagggtgtac ctgagtcttt ctggccattg cctggcagct      2160
ttgcccatgt catttattgt cagagcttca cgggaaaatg caagtagccg acttcggagc      2220
tctgagctct ggagtataat aagtcaaaag gtaaagttta ataatgata agtttgcaat       2280 aattattatt ttggccagag gcctgggaat aggggaagct tgaaactctg ggggaacaat      2340
tataattctt gattctttgt gtgatgtggg tattgttttg aatttgattt ggcaacgatt      2400
atacaatgtc tttttttcct atctgcattt ggagtatcaa taaaagactg gggcaagaga      2460
aaaaaaaaaa aaaaaaaaaa aaaaaaaaaa aaaaaaaaa aaaaaaaaaa aaaaaaaaaa       2520
aaaaaaaaaa aaaa                                                        2534

<210> SEQ ID NO 15
<211> LENGTH: 2102
<212> TYPE: DNA
<213> ORGANISM: Homo sapiens

<400> SEQUENCE: 15
acacccagct gcctgagacc ctccttcaac ctccctagag gacagcccca ctctgcctcc        60
tgctccccca gggcagcacc atgtggcccc tgtggctctg ctgggcactc tgggtgctgc       120
ccctggctgg ccccggggcg ccctgaccg aggagcagct cctgggcagc ctgctgcggc        180
agctgcagct cagcgaggtg cccgtactgg acagggccga catggagaag ctggtcatcc       240
ccgcccacgt gagggcccag tatgtagtcc tgctgcggcg cagccacggg gaccgctccc       300
gcggaaagag gttcagccag agcttccgag aggtggccgg caggttcctg gcgtcggagg       360
ccagcacaca cctgctggtg ttcggcatgg agcagcggct gccgcccaac agcgagctgg       420
tgcaggccgt gctgcggctc ttccaggagc cggtcccaa ggccgcgctg cacaggcacg        480
ggcggctgtc cccgcgcagc gcccaggccc gggtgaccgt cgagtggctg cgcgtccgcg       540
acgacggctc caaccgcacc tccctcatcg actccaggct ggtgtccgtc cacgagagcg       600
gctggaaggc cttcgacgtg accgaggccg tgaacttctg gcagcagctg agccggcccc       660
ggcagccgct gctgctacag gtgtcggtgc agagggagca tctgggcccg ctggcgtccg       720
gcgcccacaa gctggtccgc tttgcctcgc aggggcgcc agccgggctt ggggagcccc        780
agctggagct gcacaccctg gacctcaggg actatggagc tcagggcgac tgtgaccctg       840
aagcaccaat gaccgagggc acccgctgct gccgccagga gatgtacatt gacctgcagg       900
ggatgaagtg ggccaagaac tgggtgctgg agccccggg cttcctggct tacgagtgtg        960
tgggcacctg ccagcagccc ccggaggccc tggccttcaa ttggccattt ctggggccgc      1020
gacagtgtat cgcctcggag actgcctcgc tgcccatgat cgtcagcatc aaggagggag      1080
gcaggaccag gccccaggtg gtcagcctgc ccaacatgag ggtgcagaag tgcagctgtg      1140
cctcggatgg ggcgctcgtg ccaaggaggc tccagccata ggcgcctggt gtatccattg      1200
agccctctaa ctgaacgtgt gcatagaggt ggtcttaatg taggtcttaa ctttatactt      1260
agcaagttac tccatcccaa tttagtgctc ctgtgtgacc ttcgccctgt gtccttccat      1320
ttcctgtctt tcccgtccat cacccatcct aagcacttac gtgagtaaat aatgcagctc      1380
agatgctgag ctctagtagg aaatgctggc atgctgatta caagatacag ctgagcaatg      1440
```

-continued

| | |
|---|---|
| cacacatttt cagctgggag tttctgttct ctggcaaatt cttcactgag tctggaacaa | 1500 |
| taatacccta tgattagaac tggggaaaca gaactgaatt gctgtgttat atgaggaatt | 1560 |
| aaaaccttca aatctctatt tcccccaaat actgacccat tctggacttt tgtaaacata | 1620 |
| cctaggcccc tgttcccctg agagggtgct aagaggaagg atgaagggct tcaggctggg | 1680 |
| ggcagtggac agggaattgg gatacctgga ttctggttct gacagggcca caagctagga | 1740 |
| tctctaacaa cgcagaaagg ctttggctcg tcatttcctc ttaaaaagga ggagctgggc | 1800 |
| ttcagctcta agaacttcat tgccctgggg atcagacagc ccctacctac ccctgcccac | 1860 |
| tcctctggag actgagcctt gcccgtgcat atttaggtca tttcccacac tgtcttagag | 1920 |
| aacttgtcac cagaaaccac atgtatttgc atgttttttg ttaatttagc taaagcaatt | 1980 |
| gaatgtagat actcagaaga aataaaaaat gatgtttcaa aaaaaaaaaa aaaaaaaaaa | 2040 |
| aaaaaaaaaa aaaaaaaaaa aaaaaaaaaa aaaaaaaaaa aaaaaaaaaa aaaaaaaaaa | 2100 |
| aa | 2102 |

<210> SEQ ID NO 16
<211> LENGTH: 1647
<212> TYPE: DNA
<213> ORGANISM: Homo sapiens

<400> SEQUENCE: 16

| | |
|---|---|
| gcctgagacc ctcctgcagc cttctcaagg acagcccca ctctgcctct tgctcctcca | 60 |
| gggcagcacc atgcagcccc tgtggctctg ctgggcactc tgggtgttgc ccctggccag | 120 |
| ccccggggcc gccctgaccg gggagcagct cctgggcagc ctgctgcggc agctgcagct | 180 |
| caaagaggtg cccacccctgg acagggccga catggaggag ctggtcatcc ccacccacgt | 240 |
| gagggcccag tacgtggccc tgctgcagcg cagccacggg gaccgctccc gcggaaagag | 300 |
| gttcagccag agcttccgag aggtggccgg caggttcctg cgttggagg ccagcacaca | 360 |
| cctgctggtg ttcggcatgg agcagcggct gccgcccaac agcgagctgg tgcaggccgt | 420 |
| gctgcggctc ttccaggagc cggtcccaa ggccgcgctg cacaggcacg gcggctgtc | 480 |
| cccgcgcagc gcccgggccc gggtgaccgt cgagtggctg cgcgtccgcg acgacggctc | 540 |
| caaccgcacc tccctcatcg actccaggct ggtgtccgtc cacgagagcg gctggaaggc | 600 |
| cttcgacgtg accgaggccg tgaacttctg gcagcagctg agccggcccc ggcagccgct | 660 |
| gctgctacag gtgtcggtgc agaggagca tctgggcccg ctggcgtccg cgcccacaa | 720 |
| gctggtccgc tttgcctcgc aggggggcgcc agccgggctt ggggagcccc agctggagct | 780 |
| gcacaccctg gaccttgggg actatggagc tcagggcgac tgtgaccctg aagcaccaat | 840 |
| gaccgagggc acccgctgct gccgccagga gatgtacatt gacctgcagg ggatgaagtg | 900 |
| ggccgagaac tgggtgctgg agccccggg cttcctggct tatgagtgtg tgggcacctg | 960 |
| ccggcagccc ccggaggccc tggccttcaa gtggccgttt ctggggcctc gacagtgcat | 1020 |
| cgcctcggag actgactcgc tgcccatgat cgtcagcatc aaggagggag gcaggaccag | 1080 |
| gcccccaggtg gtcagcctgc ccaacatgag ggtgcagaag tgcagctgtg cctcggatgg | 1140 |
| tgcgctcgtg ccaaggaggc tccagccata ggcgcctagt gtagccatcg agggacttga | 1200 |
| cttgtgtgtg tttctgaagt gttcgagggt accaggagag ctggcgatga ctgaactgct | 1260 |
| gatggacaaa tgctctgtgc tctctagtga gccctgaatt tgcttcctct gacaagttac | 1320 |
| ctcacctaat ttttgcttct caggaatgag aatctttggc cactgagag cccttgctca | 1380 |

```
gtttctctcta ttcttattat tcactgcact atattctaag cacttacatg tggagatact    1440
gtaacctgag ggcagaaagc ccaatgtgtc attgtttact tgtcctgtca ctggatctgg    1500
gctaaagtcc tccaccacca ctctggacct aagacctggg gttaagtgtg ggttgtgcat    1560 cccaatcca gataataaag actttgtaaa acatgaataa aacacatttt attctaaaaa    1620
aaaaaaaaaa aaaaaaaaaa aaaaaaa                                         1647
```

```
<210> SEQ ID NO 17
<211> LENGTH: 85
<212> TYPE: PRT
<213> ORGANISM: Homo sapiens

<400> SEQUENCE: 17

Cys Lys Thr Gln Pro Leu Arg Gln Thr Val Ser Glu Glu Gly Cys Arg
 1               5                  10                  15

Ser Arg Thr Ile Leu Asn Arg Phe Cys Tyr Gly Gln Cys Asn Ser Phe
                20                  25                  30

Tyr Ile Pro Arg His Val Lys Lys Glu Glu Glu Ser Phe Gln Ser Cys
            35                  40                  45

Ala Phe Cys Lys Pro Gln Arg Val Thr Ser Val Leu Val Glu Leu Glu
        50                  55                  60

Cys Pro Gly Leu Asp Pro Pro Phe Arg Leu Lys Lys Ile Gln Lys Val
65                  70                  75                  80

Lys Gln Cys Arg Cys
            85

<210> SEQ ID NO 18
<211> LENGTH: 85
<212> TYPE: PRT
<213> ORGANISM: Homo sapiens

<400> SEQUENCE: 18

Cys Lys Thr Gln Pro Leu Lys Gln Thr Ile His Glu Glu Gly Cys Asn
 1               5                  10                  15

Ser Arg Thr Ile Ile Asn Arg Phe Cys Tyr Gly Gln Cys Asn Ser Phe
                20                  25                  30

Tyr Ile Pro Arg His Ile Arg Lys Glu Glu Gly Ser Phe Gln Ser Cys
            35                  40                  45

Ser Phe Cys Lys Pro Lys Lys Phe Thr Thr Met Met Val Thr Leu Asn
        50                  55                  60

Cys Pro Glu Leu Gln Pro Pro Thr Lys Lys Arg Val Thr Arg Val
65                  70                  75                  80

Lys Gln Cys Arg Cys
            85

<210> SEQ ID NO 19
<211> LENGTH: 80
<212> TYPE: PRT
<213> ORGANISM: Homo sapiens

<400> SEQUENCE: 19

Cys Arg Thr Val Pro Phe Ser Gln Thr Ile Thr His Glu Gly Cys Glu
 1               5                  10                  15

Lys Val Val Val Gln Asn Asn Leu Cys Phe Gly Lys Cys Gly Ser Val
                20                  25                  30

His Phe Pro Gly Ala Ala Gln His Ser His Thr Ser Cys Ser His Cys
            35                  40                  45
```

```
Leu Pro Ala Lys Phe Thr Thr Met His Leu Pro Leu Asn Cys Thr Glu
 50                  55                  60

Leu Ser Ser Val Ile Lys Val Val Met Leu Val Glu Glu Cys Gln Cys
 65                  70                  75                  80

<210> SEQ ID NO 20
<211> LENGTH: 89
<212> TYPE: PRT
<213> ORGANISM: Homo sapiens

<400> SEQUENCE: 20

Cys Glu Ala Lys Asn Ile Thr Gln Ile Val Gly His Ser Gly Cys Glu
 1               5                  10                  15

Ala Lys Ser Ile Gln Asn Arg Ala Cys Leu Gly Gln Cys Phe Ser Tyr
                20                  25                  30

Ser Val Pro Asn Thr Phe Pro Gln Ser Thr Glu Ser Leu Val His Cys
             35                  40                  45

Asp Ser Cys Met Pro Ala Gln Ser Met Trp Glu Ile Val Thr Leu Glu
 50                  55                  60

Cys Pro Gly His Glu Glu Val Pro Arg Val Asp Lys Leu Val Glu Lys
 65                  70                  75                  80

Ile Leu His Cys Ser Cys Gln Ala Cys
                85

<210> SEQ ID NO 21
<211> LENGTH: 72
<212> TYPE: PRT
<213> ORGANISM: Homo sapiens

<400> SEQUENCE: 21

Cys Pro Val Leu Tyr Ala Trp Asn Asp Leu Gly Ser Arg Phe Trp Pro
 1               5                  10                  15

Arg Tyr Val Lys Val Gly Ser Cys Cys Ser Val Pro Glu Gly Met Val
                20                  25                  30

Cys Lys Pro Ser Lys Ser Val His Leu Thr Val Leu Arg Trp Arg Cys
             35                  40                  45

Gln Arg Arg Gly Gly Gln Arg Cys Gly Trp Pro Ile Gln Tyr Pro Ile
 50                  55                  60

Ile Ser Glu Cys Lys Cys Ser Cys
 65                  70

<210> SEQ ID NO 22
<211> LENGTH: 104
<212> TYPE: PRT
<213> ORGANISM: Homo sapiens

<400> SEQUENCE: 22

Cys Asp Pro Glu Ala Pro Met Thr Glu Gly Thr Arg Cys Cys Arg Gln
 1               5                  10                  15

Glu Met Tyr Ile Asp Leu Gln Gly Met Lys Trp Ala Lys Asn Trp Val
                20                  25                  30

Leu Glu Pro Pro Gly Phe Leu Ala Tyr Glu Cys Val Gly Thr Cys Gln
             35                  40                  45

Gln Pro Pro Glu Ala Leu Ala Phe Asn Trp Pro Phe Leu Gly Pro Arg
 50                  55                  60

Gln Cys Ile Ala Ser Glu Thr Ala Ser Leu Pro Met Ile Val Ser Ile
 65                  70                  75                  80

Lys Glu Gly Gly Arg Thr Arg Pro Gln Val Val Ser Leu Pro Asn Met
```

```
                    85                  90                  95

Arg Val Gln Lys Cys Ser Cys Ala
            100

<210> SEQ ID NO 23
<211> LENGTH: 82
<212> TYPE: PRT
<213> ORGANISM: Homo sapiens

<400> SEQUENCE: 23

Cys Lys Arg His Pro Leu Tyr Asp Phe Ser Asp Val Gly Trp Asn Asp
1               5                   10                  15

Trp Ile Val Ala Pro Pro Gly Tyr His Ala Phe Tyr Cys His Gly Glu
            20                  25                  30

Cys Pro Phe Pro Leu Ala Asp His Ser Lys Ile Pro Lys Ala Cys Cys
        35                  40                  45

Val Pro Thr Glu Leu Ser Ala Ile Ser Met Leu Tyr Leu Asp Glu Asn
    50                  55                  60

Glu Lys Val Val Leu Lys Asn Tyr Gln Asp Met Val Val Glu Gly Cys
65                  70                  75                  80

Gly Cys

<210> SEQ ID NO 24
<211> LENGTH: 95
<212> TYPE: PRT
<213> ORGANISM: Homo sapiens

<400> SEQUENCE: 24

Cys Asp Glu His Ser Thr Glu Ser Arg Cys Cys Arg Tyr Pro Leu Thr
1               5                   10                  15

Asp Phe Glu Glu Ala Pro Gly Trp Asp Trp Ile Ile Ala Pro Lys Arg
            20                  25                  30

Tyr Lys Ala Asn Tyr Cys Ser Gly Glu Cys Glu Phe Val Phe Leu Gln
        35                  40                  45

Lys Tyr Pro His Pro Arg Gly Ser Ala Gly Pro Cys Cys Thr Pro Thr
    50                  55                  60

Lys Met Ser Pro Ile Asn Met Leu Tyr Phe Asn Gly Lys Glu Gln Ile
65                  70                  75                  80

Ile Tyr Gly Lys Ile Pro Ala Met Val Val Asp Arg Cys Gly Cys
            85                  90                  95

<210> SEQ ID NO 25
<211> LENGTH: 95
<212> TYPE: PRT
<213> ORGANISM: Homo sapiens

<400> SEQUENCE: 25

Cys Phe Ser Ser Thr Glu Lys Asn Cys Cys Val Arg Gln Leu Tyr Ile
1               5                   10                  15

Asp Phe Arg Lys Asp Leu Gly Trp Lys Trp Ile His Glu Pro Lys Gly
            20                  25                  30

Tyr His Ala Asn Phe Cys Leu Gly Pro Cys Pro Tyr Ile Trp Ser Leu
        35                  40                  45

Asp Thr Gln Tyr Pro Gly Ala Ser Ala Ala Pro Cys Cys Val Pro Gln
    50                  55                  60

Ala Leu Glu Pro Leu Pro Ile Val Tyr Tyr Val Gly Arg Lys Pro Lys
65                  70                  75                  80
```

```
Val Glu Gln Leu Ser Asn Met Ile Val Arg Ser Cys Lys Cys Ser
            85                  90                  95

<210> SEQ ID NO 26
<211> LENGTH: 75
<212> TYPE: PRT
<213> ORGANISM: Homo sapiens

<400> SEQUENCE: 26

Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro
65                  70                  75

<210> SEQ ID NO 27
<211> LENGTH: 70
<212> TYPE: PRT
<213> ORGANISM: Homo sapiens

<400> SEQUENCE: 27

Ala Leu Leu Cys Ala Cys Thr Ser Cys Leu Gln Ala Asn Tyr Thr Cys
1               5                   10                  15

Glu Thr Asp Gly Ala Cys Met Val Ser Ile Phe Asn Leu Asp Gly Met
            20                  25                  30

Glu His His Val Arg Thr Cys Ile Pro Lys Val Glu Leu Val Pro Ala
        35                  40                  45

Gly Lys Pro Phe Tyr Cys Leu Ser Ser Glu Asp Leu Arg Asn Thr His
    50                  55                  60

Cys Cys Tyr Thr Asp Tyr
65                  70

<210> SEQ ID NO 28
<211> LENGTH: 354
<212> TYPE: PRT
<213> ORGANISM: Homo sapiens
<220> FEATURE:
<221> NAME/KEY: VARIANT
<222> LOCATION: 113
<223> OTHER INFORMATION: Xaa = Thr or Gly

<400> SEQUENCE: 28

Leu Thr Glu Glu Gln Leu Leu Gly Ser Leu Leu Arg Gln Leu Gln Leu
1               5                   10                  15

Ser Glu Val Pro Val Leu Asp Arg Ala Asp Met Glu Lys Leu Val Ile
            20                  25                  30

Pro Ala His Val Arg Ala Gln Tyr Val Val Leu Leu Arg Arg Ser His
        35                  40                  45

Gly Asp Arg Ser Arg Gly Lys Arg Phe Ser Gln Ser Phe Arg Glu Val
    50                  55                  60

Ala Gly Arg Phe Leu Ala Ser Glu Ala Ser Thr His Leu Leu Val Phe
65                  70                  75                  80

Gly Met Glu Gln Arg Leu Pro Pro Asn Ser Glu Leu Val Gln Ala Val
            85                  90                  95
```

-continued

```
Leu Arg Leu Phe Gln Glu Pro Val Pro Lys Ala Ala Leu Asn His Arg
            100                 105                 110

Xaa His Gly Arg Asn Leu Ser Pro Arg Ser Ala Gln Ala Arg Val Thr
        115                 120                 125

Val Glu Trp Leu Arg Val Arg Asp Asp Gly Ser Asn Arg Thr Ser Leu
    130                 135                 140

Ile Asp Ser Arg Leu Val Ser Val His Glu Ser Gly Trp Lys Ala Phe
145                 150                 155                 160

Asp Val Thr Glu Ala Val Asn Phe Trp Gln Gln Leu Ser Arg Pro Arg
                165                 170                 175

Gln Pro Leu Leu Leu Gln Val Ser Val Gln Arg Glu His Leu Gly Pro
            180                 185                 190

Leu Ala Ser Gly Ala His Lys Leu Val Arg Phe Ala Ser Gln Gly Ala
            195                 200                 205

Pro Ala Gly Leu Gly Glu Pro Gln Leu Glu Leu His Thr Leu Asp Leu
    210                 215                 220

Arg Asp Tyr Gly Ala Gln Gly Asp Cys Asp Pro Glu Ala Pro Asn Met
225                 230                 235                 240

Thr Glu Asn Gly Thr Arg Cys Cys Arg Gln Glu Met Tyr Ile Asp Leu
                245                 250                 255

Gln Gly Met Lys Trp Ala Lys Asn Trp Val Leu Glu Pro Pro Gly Phe
            260                 265                 270

Leu Ala Tyr Glu Cys Val Gly Thr Cys Gln Gln Pro Pro Glu Ala Asn
            275                 280                 285

Leu Ala Thr Phe Asn Trp Ser Pro Thr Phe Leu Gly Pro Arg Gln Cys
            290                 295                 300

Ile Ala Ser Glu Thr Ala Ser Leu Pro Met Ile Val Ser Ile Lys Glu
305                 310                 315                 320

Gly Gly Arg Thr Arg Pro Gln Val Val Ser Leu Pro Asn Met Arg Val
                325                 330                 335

Gln Lys Cys Ser Cys Ala Ser Asp Gly Ala Leu Val Pro Arg Arg Leu
            340                 345                 350

Gln Pro
```

LEFTY POLYPEPTIDES AND DERIVATIVES THEREOF

RELATED APPLICATION

This application claims the benefit of Provisional Application No. 60/696,226, filed Jul. 1, 2005, which is incorporated by reference herein.

BACKGROUND OF THE INVENTION

Myostatin, or growth/differentiation factor 8 (GDF-8), belongs to the transforming growth factor-β (TGF-β) superfamily (McPherron et al., Nature 387:83-90 (1997)). The human myostatin gene has been cloned (Nestor et al. Proc. Natl. Acad. Sci. 95:14938-43 (1998)). Myostatin is present in human skeletal muscle in both type 1 and type 2 fibers. Myostatin negatively regulates the growth and development of skeletal muscle (Nestor et al., supra).

Myostatin knock-out mice are significantly larger than wild-type mice and have a large and widespread increase in skeletal muscle mass (McPherron et al., Nature 387:83-90 (1997). Two breeds of cattle, characterized by increased muscle mass, have mutations in the myostatin coding sequence (McPherron et al., Proc. Natl. Acad. Sci. 94:12457-61 (1997)). The serum and intramuscular concentrations of immunoreactive myostatin are increased in HIV-infected men with muscle wasting compared with healthy men, and correlate inversely with the fat-free mass index (Nestor et al., supra). Recently, a human child with an apparent loss-of-function mutation in myostatin was identified (Schuelke et al., N Engl J Med. 2004 Jun. 24; 350(26):2682-8). The infant had a marked increase in skeletal muscle mass. Taken together, these data provide genetic and physiological evidence that myostatin is a negative regulator of skeletal muscle growth in humans and contributes to muscle wasting in HIV-infected men.

In view of the above findings, a need exists for a manner of regulating myostatin activity, particularly in individuals who experience muscle wasting as a result of a condition or disease state such as, for example, aging, Autoimmune Deficiency Syndrome (AIDS), Multiple Sclerosis, and cancer. Additionally, GDF-11 is a protein that is closely related to myostatin and participates in neurological functions. Thus, regulators of myostatin are likely to find use in the regulation of GDF-11 and neurological processes as well.

The present invention provides methods and compositions which may be utilized to help individuals with a variety of conditions associated with signaling mediated by TGF-β family members, including myostatin and GDF-11.

SUMMARY OF THE INVENTION

The disclosure provides new uses for Lefty polypeptides and provides a variety of Lefty derivative polypeptides. In part, the disclosure provides methods for using Lefty polypeptides as antagonists of myostatin and/or GDF-11. Accordingly, the disclosure provides methods for using Lefty polypeptides to treat a host of disorders related muscle or neurological function. In part, the disclosure provides regions of Lefty polypeptides that are functionally significant for the inhibition of Nodal, myostatin and/or GDF-11, and regions that may be readily modified without substantially affecting the inhibition of Nodal, myostatin and/or GDF-11. Therefore, the disclosure provides Lefty derivative polypeptides that retain Nodal, myostatin and/or GDF-11 antagonist function. Lefty derivative polypeptides may also exhibit desirable features such as improved solubility or improved pharmacokinetics.

In certain aspects, the disclosure provides recombinant Lefty derivative polypeptides. Lefty derivative polypeptides are polypeptides that bear structural and functional relationship to naturally occurring Lefty polypeptides but have an amino acid sequence that is not identical to that of the mouse Lefty-1 and Lefty-2 polypeptides or the human Lefty-A or Lefty-B polypeptides. Lefty derivative polypeptides retain the ability to bind to one or more of Nodal, myostatin and/or GDF-11. In particular, the disclosure provides that Lefty proteins may be viewed as containing five regions, Regions 1-5. See FIGS. 1-5. The general cystine knot structure (maintained primarily by a series of cross-linked cysteine residues) and Regions 2 and 4 are expected to be primarily responsible for the binding of Lefty to Nodal, myostatin and GDF-11. Regions 1, 3 and 5, and particularly the C-terminal portion of Region 1 and Region 3 as a whole, are not expected to participate significantly in binding, and accordingly, these regions are attractive targets for modifying the amino acid sequences of Lefty proteins. Preferably, recombinant Lefty derivative polypeptides are selected to inhibit signaling mediated by a protein such as an ActRII receptor, myostatin, Nodal, and/or GDF-11 in a biochemical binding assay or a cell-based assay.

In certain embodiments, a recombinant Lefty derivative polypeptide comprises an amino acid sequence as set forth in the formula: -A-X-B-, wherein A consists of an amino acid sequence at least 85%, 90%, 95%, 98% or 100% identical to the sequence of Region 2 of human Lefty A (SEQ ID NO:5) or Lefty B (SEQ ID NO:7); and wherein B consists of an amino acid sequence at least 85%, 90%, 95%, 98% or 100% identical to the sequence of Region 4 of human Lefty A or B, SEQ ID Nos: 6 and 8, respectively. Region 2 of Lefty A has the sequence CRQEMYIDLQGMKWAKNWVLEPPG FLAYECVGT (SEQ ID NO: 5). Region 2 of Lefty B has the sequence CRQEMYIDLQGMKWAENWVLEPPG-FLAYECVGT (SEQ ID NO: 7). Region 4 of Lefty A has the sequence CIASETASLPMIVSIKEGGRTRPQVVS-LPNMRVQKC (SEQ ID NO: 6) and Region 4 of Lefty B has the sequence CIASETDSLPMIVSIKEGGRTRPQVVS-LPNMRVQKC (SEQ ID NO: 8).

A recombinant Lefty derivative polypeptide will preferably bind to one or more of Nodal, myostatin and GDF-11, preferably with a $K_D$ of less than $10^{-6}$, $10^{-7}$, $10^{-8}$ or $10^{-9}$. X may consist of zero, one or more than one amino acid, except that X should be selected so as to maintain the functional activity of the Lefty derivative polypeptide. X may comprise an amino acid sequence that has low immunogenicity. X may include a site for post-translational modification, preferably glycosylation. X may be less than 500, 400, 300, 200, 100, 50 or less than 25 amino acids. X may include an additional domain, such as a dimerization domain, a domain that binds to Nodal, myostatin and/or GDF-11 or a domain that otherwise confers a desirable property such as improved solubility or improved pharmacokinetics.

A recombinant Lefty derivative polypeptide may or may not include amino acids that are N-terminal to the A portion of the -A-X-B- formula, and also may or may not include amino acids that are C-terminal to the B portion of the -A-X-B- formula. Accordingly, a Lefty derivative polypeptide comprising a sequence of formula -A-X-B- should be understood to include, as optional embodiments, sequence that is N-terminal to A and/or sequence that is C-terminal to B. If specific reference to these portions is needed, such regions may be referred to as "W" and "Y". Thus, a derivative Lefty polypeptide may consist essentially of a sequence represented as W-A-X-B, A-X-B-Y or W-A-X-B-Y. The sequence of W and Y, if such sequence is included at all, is relatively unconstrained and will be selected so as to retain any of the desirable functional activities of the Lefty derivative polypeptide. W and Y may comprise an amino acid sequence that has low immunogenicity. W and Y may include a site for post-translational modification, preferably glycosylation. W and Y may be less than 500, 400, 300, 200, 100, 50 or less than 25 amino acids. W and Y may include an additional domain, such as a dimerization domain, a domain that binds to Nodal, myostatin and/or GDF-11 or a domain that otherwise confers a desirable property such as improved solubility or improved pharmacokinetics. In one embodiment, W includes a "long" Region 1 sequence corresponding to the sequence resulting after cleavage of the most N-terminal RXXR propeptide cleavage site of a Lefty protein. In one embodiment, W includes a "short" sequence corresponding to the sequence resulting after cleavage of the second RXXR propeptide cleavage site. In further embodiments, W may include some or all of the propeptide sequence, in which case W will generally be altered such that the first and/or second RXXR cleavage site is altered to reduce or eliminate cleavage. A preferred method for altering the RXXR cleavage site is to include a site for glycosylation which site either alters the sequence of the RXXR site or results in a glycosylation that occludes the cleavage site or otherwise inhibits cleavage. Any of portions W, X or Y may be at least 85% identical to a naturally occurring region 1, 3 or 5, respectively, of a naturally occurring Lefty polypeptide, particularly human Lefty A or B, and may also be at least 90%, 95%, 98%, 99% or 100% identical to such sequence.

The recombinant Lefty derivative polypeptide may comprise an amino acid sequence that is at least 85% identical to the cystine knot portion of a human Lefty polypeptide. The recombinant Lefty derivative polypeptide may comprise an amino acid sequence that is at least 85% identical to a human Lefty polypeptide sequence selected from the group consisting of: amino acids 22-353 of SEQ ID NO:1 and amino acids 22-353 of SEQ ID NO:2, wherein one or both RXXR cleavage sequences are altered so as to prevent cleavage at the altered sequence.

As demonstrated herein, mature Lefty A polypeptides initiating at the first or second RXXR cleavage site, and N- or C-terminal Fc fusions thereof, have myostatin binding activity. Accordingly, a recombinant Lefty polypeptide may be a "long" form (e.g., 34 kDa form) or a "short" form (e.g., 28 kDa form) depending on the size of the sequence, corresponding to Region 1, between the propeptide cleavage site and the beginning of the cystine knot domain. A long form may be a Lefty derivative polypeptide in which the second RXXR cleavage site is altered to eliminate cleavage and permit consistent production of the longer form. A long form may also be produced by expression of a sequence that retains the second RXXR cleavage site in a cell line or culture conditions that are deficient for cleavage activity.

A Lefty derivative polypeptide may include one or more sequence alterations that introduce one or more sites for post-translational modification. Glycosylation is a preferred post-translational modification, and such modification will preferably be positioned in portions W, X or Y of the Lefty derivative polypeptide.

As noted above, a Lefty derivative polypeptide may include one or more additional domains, fused to the amino- or the carboxy-terminus or within any of Regions W, X or Y. As described herein, Lefty may be a potent antagonist in a dimeric or multimeric form, and therefore, the additional domain may be a dimerization or multimerization domain. It is expected that the propeptide functions naturally to mediate Lefty dimerization, and therefore, the dimerization domain may comprise a Lefty propeptide sequence of either a short or long form. A dimerization domain may be an Fc domain. A dimerization domain may comprise an immunoglobulin Fab constant domain, and the Fab constant domain may be selected, for example, from an immunoglobulin heavy chain constant region and an immunoglobulin light chain constant region. Other dimerization or multimerization domains may be chosen, such as a leucine zipper domain. A leucine zipper domain may comprise at least four leucine heptads, and may be, for example, a Fos or a Jun leucine zipper domain. Amino acid linkers may be interposed between any Lefty amino acid sequence and any additional domain(s). An additional domain may be a domain that binds to and, preferably, inhibits Nodal, myostatin and/or GDF-11. For example, Lefty is expected to block the Type II receptor binding site of BMP proteins, and therefore a second domain that block the Type I receptor (e.g., ALK4 or ALK7) binding site would be useful to improve the antagonistic properties of the Lefty molecule. A domain that competitively inhibits the binding of Nodal, myostatin and/or GDF-11 to ALK4 or ALK7 may be, for example, (a) an extracellular portion of ALK4; (b) an extracellular portion of ALK7; (c) an antigen-binding portion of an antibody that binds Nodal, myostatin and/or GDF-11; and (d) a randomized polypeptide that has been selected for binding to Nodal, myostatin and/or GDF-11.

In certain aspects, a recombinant Lefty derivative polypeptide comprises a heterogenous sequence that mediates secretion of the recombinant Lefty derivative polypeptide, such as a honey bee melatin leader sequence.

The disclosure further provides recombinant polynucleotides comprising a nucleotide sequence encoding a Lefty derivative polypeptide disclosed herein. The recombinant polynucleotide may include a promoter sequence operably linked to the nucleotide sequence encoding the Lefty derivative polypeptide. Such nucleic acids may be introduced into cells, such as mammalian cells (e.g., human or CHO cells). Such cells may be used in a method of making a recombinant Lefty derivative polypeptide, comprising: a) culturing a cell encoding the recombinant Lefty derivative polypeptide under conditions suitable for expression of the recombinant Lefty derivative polypeptide; and b) recovering the recombinant Lefty derivative polypeptide so expressed.

As noted above, it is now expected that Lefty will act as a potent antagonist in a dimeric or multimeric form. Therefore, one may prepare an isolated Lefty polypeptide complex comprising: a first Lefty polypeptide and a second Lefty polypeptide, wherein the first and second Lefty polypeptides are associated to form a complex, and wherein the complex binds to a TGF-β family member selected from the group consisting of: myostatin, Nodal and GDF-11. The Lefty polypeptide complex may be a heterodimer (or multimer) or a homodimer (or multimers).

In certain aspects, the disclosure provides pharmaceutical preparations comprising any of the various Lefty derivatives or dimeric Lefty polypeptides.

In certain aspects, the disclosure provides new uses for Lefty polypeptides, including Lefty derivative polypeptides disclosed herein. In one embodiment, the disclosure provides methods for treating a subject having a disorder associated with muscle loss or insufficient muscle growth, comprising administering to the subject an effective amount of a composition comprising a Lefty polypeptide. In another embodiment, the disclosure provides methods for treating a disorder associated with neurodegeneration, comprising administering to the subject an effective amount of a composition comprising a Lefty polypeptide. In a further embodiment, a Lefty polypeptide may be used to promote weight loss and to treat disorders relating to body fat content or body weight, such as obesity and Type II diabetes. In certain embodiments, Lefty polypeptides may be used to bind to and/or inhibit the activity of Nodal, myostatin and/or GDF-11 in vitro or in vivo. The Lefty polypeptide may be a wildtype Lefty polypeptide or fragments thereof, a recombinant Lefty derivative polypeptide, as well as a dimerized Lefty polypeptide.

The disclosure further provides for the use of a Lefty polypeptide for making a medicament for the treatment of a disorder associated with abnormal amount, development or metabolic activity of muscle tissue or a disorder associated with neurodegeneration or a disorder relating to body fat content or body weight.

BRIEF DESCRIPTION OF THE DRAWINGS

Figure 3:
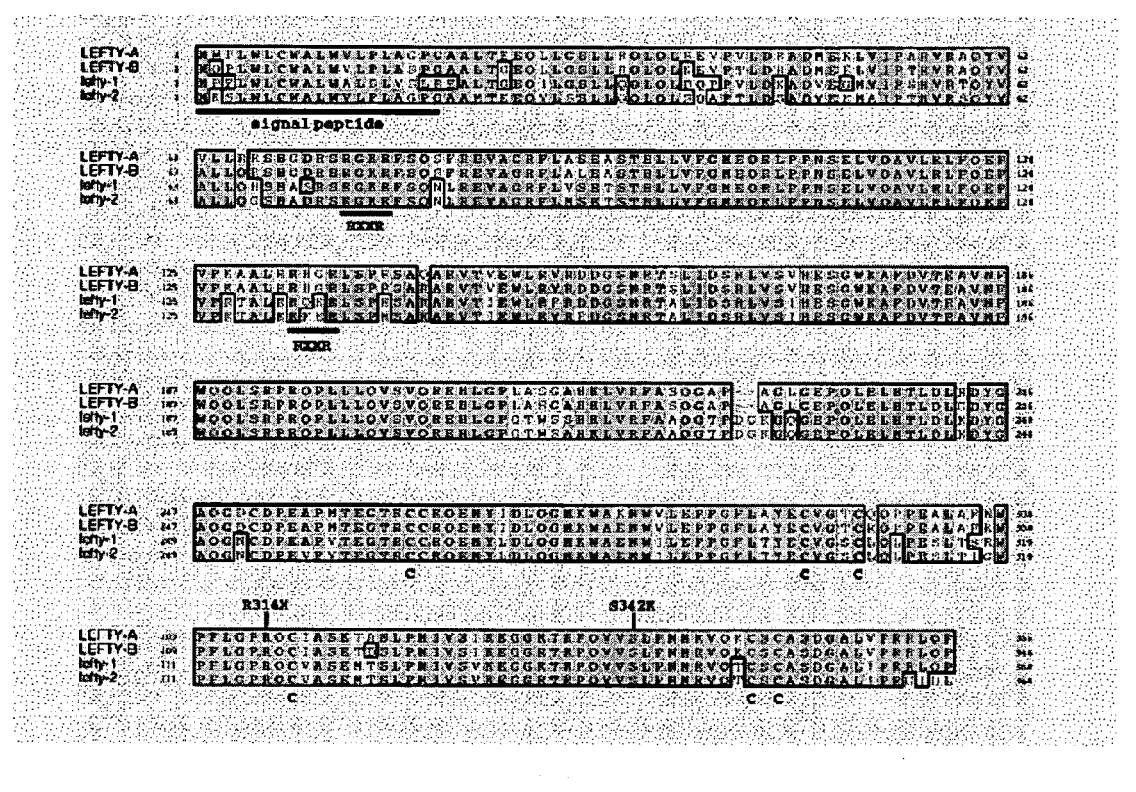

FIG. 3 shows an alignment of the Lefty proteins, human Lefty-A and -B and murine lefty-1 and lefty-2. Regions corresponding to the signal peptide, the RXXR cleavage sites (which mark the C-terminus of the propeptide), the conserved cysteines ("C") of the cystine knot and the locations of sequence variations that are associated with human disorders (R314K, S342K) are shown. SEQ ID Nos. 1-4.

FIG. 4 shows the human Lefty A and Lefty B amino acid sequences (NCBI RefSeq ID NP_003231 and NP_066277, respectively; SEQ ID Nos. 1 and 2, respectively.) The signal sequence is underlined with a dotted line. RXXR cleavage sites are underlined. The cystine knot domain is double underlined.

FIG. 5 shows the amino acid sequences of the 34 kDa mature forms of human Lefty A and Lefty B which result from cleavage at the first RXXR cleavage site (SEQ ID Nos. 9 and 10 respectively). Regions 1 through 5, as described in FIG. 1, are indicated. Regions 1 and 5 have a broken underline. Regions 2 and 4 have a single underline. Region 3 has a double underline. Shaded regions correspond to regions that may be modified or deleted to generate Lefty variants that retain Nodal, myostatin and/or GDF-11 inhibiting activity.

DETAILED DESCRIPTION OF THE INVENTION

1. Overview

Figure 1:
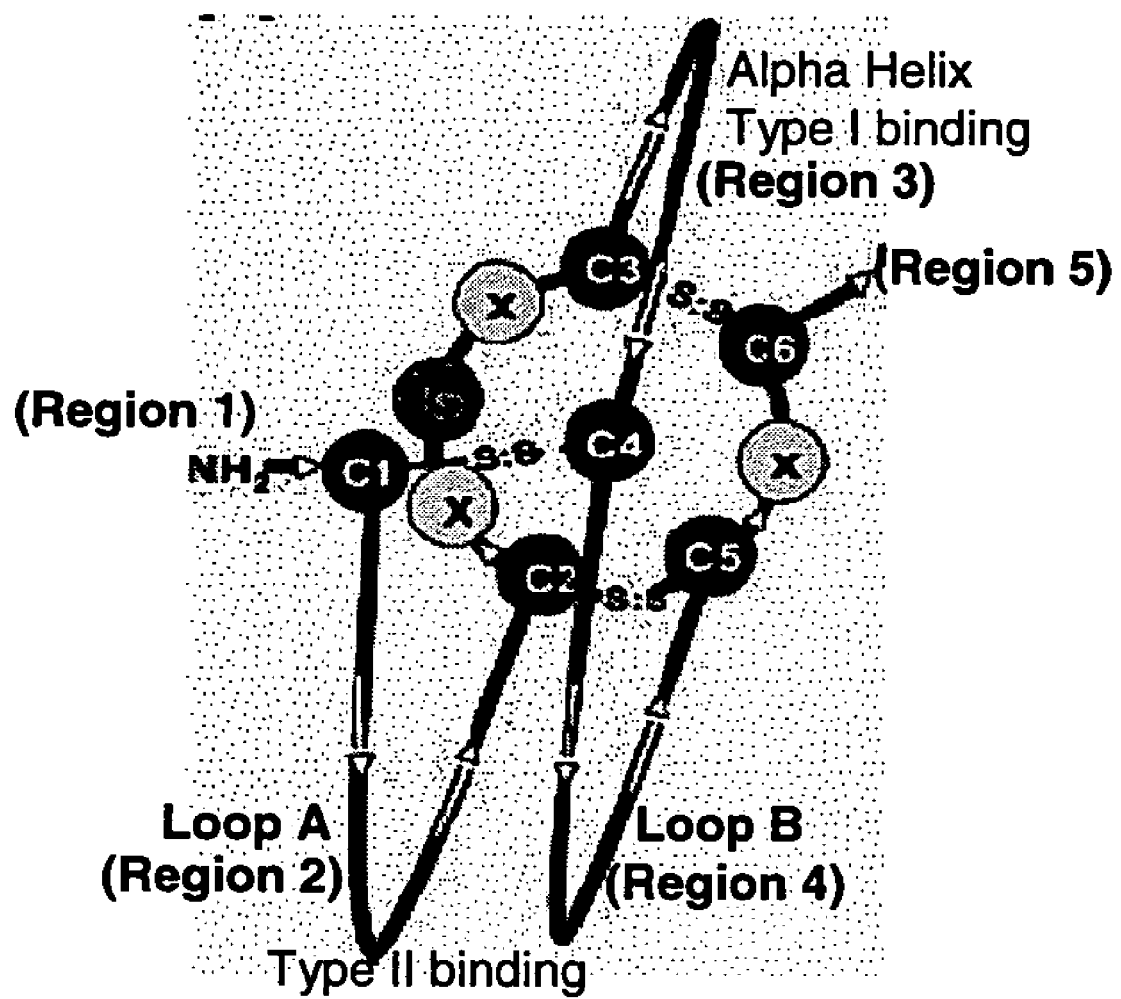
FIG. 1 shows a schematic of the conserved cystine knot structure of members of the TGF-β superfamily, based on the structure of BMP-7. Cysteines that form the core of the structure are indicated as C1-C6. In the traditional receptor ligand members of the family, Loops A and B mediate binding to Type II receptors, while the region between C3 and C4 contains an alpha helix and other amino acids that mediate dimerization and binding to Type I receptors. The region between C3 and C4 also contains a cysteine that is critical for the formation of a disulfide linkage between monomers. In the Dan family of ligand binding "traps", Loops A and B participate in binding to the target BMP ligand while the region between C3 and C4 is generally smaller than in the receptor ligands. As described herein, Lefty proteins may be mapped onto this structure and divided into five functional regions. Region 1 is the portion of the mature polypeptide that is N-terminal to C1 (the first cysteine of the cystine knot domain). Regions 2 and 4 correspond to Loops A and B and participate in ligand binding (ligands such as Nodal, myostatin and GDF-11). Region 3 of Lefty proteins lacks the alpha helix and the cysteine that participates in intermolecular crosslinking. Region 5 is the portion that is C-terminal to the final cysteine of the cystine knot domain.
Figure 2:
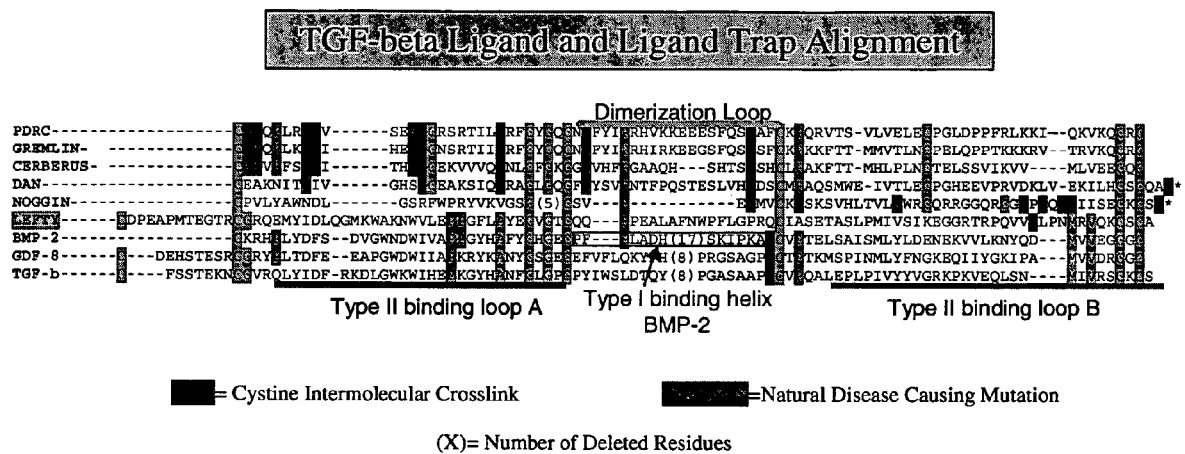
FIG. 2 shows an alignment of the cystine knot domains of several members of the TGF-β family. PDRC, Gremlin, Cerberus and Noggin are members of the ligand "trap" grouping—proteins that bind to and inhibit the activity of various receptor ligand members of the TGF-β family. BMP-2, GDF-8 and TGF-β are traditional receptor ligands that form disulfide-crosslinked dimers and bind and activate Type I and Type II receptor-mediated signaling. Lefty, shown at center, is a Lefty polypeptide. The regions corresponding to the Loops A and B, which mediate Type II receptor binding in BMP receptor ligands, are underlined at bottom. The region corresponding to the "Dimerization Loop" is overlined at top, and a box shows the Type I receptor binding helix of BMP-2. The cysteine that participates in monomer-monomer disulfide bond formation is shown in red. Notably, the Dimerization Loop is longer in BMP-2, GDF-8 and TGF-β than in Lefty or the trap family members. Conserved cysteines are shown in green. The SEQ ID Nos. for each of these sequences is as follows: PDRC (SEQ ID NO:17); Gremlin (SEQ ID NO:18); Cerberus (SEQ ID NO:19); Dan (SEQ ID NO:20); Noggin (SEQ ID NO:21); Human Lefty A (SEQ ID NO:22); BMP-2 (SEQ ID NO:23); GDF-8 (SEQ ID NO:24); TGF-β (SEQ ID NO:25).

The disclosure relates to the discovery that Lefty proteins bind to GDF-11, in addition to Nodal. Given the sequence conservation between myostatin and GDF-11, Lefty proteins are expected to bind and inhibit both myostatin and GDF-11. The disclosure also relates to the surprising insight that Lefty proteins will be potent as binders when dimerized or multimerized. Accordingly, the disclosure provides Lefty polypeptides and fusion proteins that form dimers or multimers. Furthermore, the disclosure provides regions of various Lefty polypeptides that may be modified to obtain Lefty derivatives that may retain the ability to inhibit Nodal, myostatin and/or GDF-11. Such derivatives may exhibit one or more desirable features, including, for example, improved protein expression, improved solubility, decreased tendency to adsorb non-specifically to surfaces (improved "handling"), improved serum half-life, improved tissue distribution and decreased immunogenicity.

Murine Lefty-1 and Lefty-2 genes are expressed asymmetrically prior to the appearance of anatomic left-right (LR) differences (Meno C, et al., 1996, Nature 381:151-155; Meno C, et al., 1997, Genes Cells 2:513-524; Meno C, et al., 1998, Cell, 94:287-297). Both are expressed on the left side of the embryo in the floor-plate and in the lateral-plate mesoderm; Lefty-2 is expressed more strongly in lateral-plate mesoderm than in floor-plate, whereas the reverse is true for Lefty-1. Two human Lefty proteins, Lefty-A and Lefty-B, were identified as homologous to the murine proteins (Kosaki et al., 1999, Am J Hum Genet, 64:712-721). In humans, two mutations in Lefty-A are associated with left-right axis malformations. Lefty-A is also referred to as Ebaf (endometrum bleeding-associated factor) (Kothapalli et al., 1997, J Clin Invest, 99:2342-2350). Human Lefty-A and Lefty-B are 96% identical in amino acid sequence. Mouse lefty-1 and lefty-2 are 90% identical in amino acid sequence. Human Lefty-A is 81% identical to each of the mouse lefty proteins, and human Lefty-B is 82% identical to each of the mouse lefty proteins.

TGF-β family members are generally encoded as preproproteins that undergo secretion and cleavage to remove a signal sequence and further cleavage at a dibasic or RXXR site, which breaks the peptide bond between the mature carboxy-terminal portion and the amino-terminal propeptide region. Lefty proteins have two, rather than one, putative cleavage sites that release carboxy-terminal mature protein, and multiple cleavage forms of Lefty can be found in cell cultures. As shown herein, both long (34 kDa) and short (28 kDa) forms of mature Lefty retain certain key activities. Among members of the TGF-β family, propeptides have different functional attributes. In some instances, the propeptide portion is released upon cleavage and plays no further functional role. In other instances, the propeptide portion associates with the mature protein, generally either increasing bioavailability of the mature portion or inhibiting the activity of the mature portion, or both. No role for the Lefty propeptide has been proposed. However, in view of the present disclosure it is expected that, in physiological conditions, the propeptide region of Lefty polypeptides may associate with the mature portion and mediate the formation of dimers.

The mature portions of TGF-β family members generally contain a conserved cystine-knot structure. This structure is illustrated in FIG. 1, as deduced from the solved structure of BMP-7. The cystine knot include two loops, designated Loop 1 and Loop 2, that participate in type II receptor binding. A third region contains amino acids that participate in Type I receptor binding and an α-helix and a conserved cysteine that are usually essential for formation of homo- or hetero-dimers and the covalent stabilization of such dimers (Thisse C, et al., 1999, Development, 126:229-240; Meno C, et al., 1996, Nature 381:151-155; Meno C, et al., 1997, Genes Cells 2:513-524). The binding of TGF-β ligand to the Type I and Type II receptors normally activates the canonical TGF-β signaling pathway, typically marked by activation of one or more SMAD proteins. Lefty proteins are atypical members of the TGF-β family. Unlike most other TGF-β family members, Lefty proteins lack the α-helix and a conserved cysteine that mediate dimerization. For these reasons, most published reports indicate that Lefty proteins are monomeric (see, e.g., Sakuma et al., 2002). Thus, it is a surprising insight of the present disclosure that Lefty proteins bind to target molecules in a dimeric form and may naturally perform their physiological roles in a dimeric conformation.

Numerous members of the TGF-β family act as antagonists of the canonical TGF-β receptor-ligand signaling pathway. The Dan family of antagonists have a conserved cystine knot domain. These proteins dimerize and bind to a target ligand of the TGF-β family, inhibiting the signaling mediated by that ligand. Another antagonist, Noggin, functions similarly. These antagonists are referred to herein as "traps".

Lefty also acts as an antagonist. Genetic evidence suggests that Lefty functions as an antagonist of Nodal. In embryonic patterning, Lefty is thought to restrict the range and duration of Nodal activity (e.g., Meno C, et al., 1999, Mol Cell, 4:287-298). Lefty-induced inhibition of Nodal signaling was rescued by excess ActRIIA or ActRIIB, suggesting that Lefty antagonizes Nodal signaling through competive binding to the common receptor ActRIIA or ActRIIB (Sakuma et al., 2002, Genes Cells 7:401-412). This mode of antagonism is consistent with the presumed monomeric nature of Lefty, and presents a model for antagonism that is distinct from the mechanism proposed for the "trap" proteins. In one report, Lefty was reported to bind directly to Nodal (Chen and Shen, 2004, Curr. Biol. 14: 618-624).

The present disclosure reports the discovery that Lefty may directly bind to and antagonize numerous ligands of the TGF-β family, and may do so as a dimer. Accordingly, the disclosure provides Lefty polypeptides for inhibiting Nodal, myostatin (GDF-8) and/or GDF-11 function. The present disclosure further provides Lefty polypeptide derivatives, meaning variants and fragments of naturally occurring Lefty polypeptides that retain the ability to inhibit Nodal, myostatin and/or GDF-11. Examples of such derivatives include N-terminally truncated versions of Lefty, Lefty polypeptide containing alterations in any or all of Regions 1, 3 and 5 (see FIGS. 1-4), glycosylated (or other post-translationally modified) forms of Lefty and fusion proteins comprising any of the various Lefty polypeptides disclosed herein. These so-called "Lefty derivatives" can be used to reduce the severity of a pathologic condition, which is characterized, at least in part, by an undesirable level of Nodal, myostatin and/or GDF-11 activity. For instance, the pharmaceutical preparations of the present disclosure can be administered in an amount effective to prevent, ameliorate or reduce the severity of a variety of disorders related to neurological or muscular function.

The terms used in this specification generally have their ordinary meanings in the art, within the context of this disclosure and in the specific context where each term is used. Certain terms are discussed below or elsewhere in the specification, to provide additional guidance to the practitioner in describing the compositions and methods of the disclosure and how to make and use them. The scope an meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the disclosure may include steps of comparing sequences to each other, including wild-type sequence to one or more mutants/sequence variants Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Λ") in the polymer sequence not containing the inserted or deleted residue.

"Homologous" refers to the relationship between two proteins or nucleic acids that possess a common evolutionary origin, including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity" refers to the degree of identity or correspondence between nucleic acid or amino acid sequences that may or may not share a common evolutionary origin.

A nucleic acid molecule is "hybridizable" to another nucleic acid molecule, such as a cDNA, genomic DNA, or RNA, when a single stranded form of the nucleic acid molecule can anneal to the other micleic acid molecule under the appropriate conditions of temperature and solution ionic strength (see Sambrook et al. *Molecular Cloning: A Laboratory Manual*, Second Edition (1989) Cold Spring Harbor Laboratory Press, Cold Spring Harbor, N.Y.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS).

Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. SSC is 0.15 M NaCl, 0.015 M Na-citrate.

"High stringency conditions" are understood to encompass conditions of hybridization which allow hybridization of structurally related, but not structurally dissimilar, nucleic acids. The term "stringent" is a term of art which is understood by the skilled artisan to describe any of a number of alternative hybridization and wash conditions which allow annealing of only highly complementary nucleic acids.

Exemplary high stringent hybridization conditions is equivalent to about 20-27° C. below the melting temperature ($T_m$) of the DNA duplex formed in about 1 M salt. Many equivalent procedures exist and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pages 9.47-9.57 of Sambrook, et al. (1989) *Molecular Cloning, 2nd ed.*, Cold Spring Harbor Press).

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$, for hybrids of nucleic acids having those sequences. The relative stability (corresponding to higher $T_m$) of micleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.51). For hybridization with shorter nucleic acids, i.e., oligonucleotides, the position of mismatches becomes more important, and the length of the oligonucleotide determines its specificity (see Sambrook et al., supra, 11.8). A minimum length for a hybridizable nucleic acid is at least about 10 nucleotides; preferably at least about 15 nucleotides; and more preferably the length is at least about 20 nucleotides.

Unless specified, the term "standard hybridization conditions" refers to a $T_m$ of about 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

Suitable hybridization conditions for oligonucleotides (e.g., for oligonucleotide probes or primers) are typically somewhat different than for full-length nucleic acids (e.g., full-length cDNA), because of the oligonucleotides' lower melting temperature. Because the melting temperature of oligonucleotides will depend on the length of the oligonucleotide sequences involved, suitable hybridization temperatures will vary depending upon the oligonucleotide molecules used. Exemplary temperatures may be 37° C. (for 14-base oligonucleotides), 48° C. (for 17-base oligonucleotides), 55° C. (for 20-base oligonucleotides) and 60° C. (for 23-base oligonucleotides). Exemplary suitable hybridization conditions for oligonucleotides include washing in 6×SSC, 0.05% sodium pyrophosphate, or other conditions that afford equivalent levels of hybridization.

A protein or polypeptide, including an enzyme, may be a "native" or "wild-type," meaning that it occurs in nature; or it may be a "mutant," "variant," or "modified," meaning that it has been made, altered, derived, or is in some way different or changed from a native protein or from another mutant.

"Lefty protein" or "Lefty polypeptide" refers to mammalian Lefty proteins, such as the murine Lefty proteins or human Lefty proteins, and other proteins which share sequence homology and functional attributes of the mammalian Lefty proteins, including any Lefty derivatives. Exemplary amino acid sequences for Lefty proteins include:

```
Murine Lefty-1 protein (NCBI RefSeq ID NP_034224) (SEQ ID NO:3):
  1 mpflwlcwal walslvslre altgeqilgs llqqlqldqp pvldkadveg mvipshvrtq 61 yvallqhsha srsrgkrfsq nlrevagrfl vsetsthllv fgmeqrlppn selvqavlrl 121 fqepvprtal rrqkrlsphs ararvtiewl rfrddgsnrt alidsrlvsi hesgwkafdv 181 teavnfwqql srprqplllq vsvqrehlgp gtwsshklvr faaqgtpdgk gqgepqlelh 241 tldlkdygaq gncdpeapvt egtrccrqem yldlqgmkwa enwileppgf ltyecvgscl 301 qlpesltsrw pflgprqcva semtslpmiv svkeggrtrp qvvslpnmrv qtcscasdga 361 liprrlqp
```

Murine Lefty-2 protein (NCBI RefSeq ID NP_796073) (SEQ ID NO:4):
```
  1 mkslwlcwal wvlplagpga amteeqvlss llqqlqlsqa ptldsadvee maipthvrsq
 61 yvallqgsha drsrgkrfsq nfrevagrfl msetsthllv fgmeqrlppn selvqavlrl
121 fqepvprtal rrferlsphs ararvtiewl rvredgsnrt alidsrlvsi hesgwkafdv
181 teavnfwqql srprqplllq vsvqrehlgp gtwsahklvr faaqgtpdgk gqgepqlelh
241 tldlkdygaq gncdpevpvt egtrccrqem yldlqgmkwa enwileppgf ltyecvgscl
301 qlpesltigw pflgprqcva semtslpmiv svkeggrtrp qvvslpnmrv qtcscasdga
361 liprgidl
```

Human Lefty-A protein (NCBI RefSeq ID NP_003231) (SEQ ID NO:1):
```
  1 mwplwlcwal wvlplagpga alteeqllgs llrqlqlsev pvldradmek lvipahvraq
 61 yvvllrrshg drsrgkrfsq sfrevagrfl aseasthllv fgmeqrlppn selvqavlrl
121 fqepvpkaal hrhqrlsprs aqarvtvewl rvrddgsnrt slidsrlvsv hesgwkafdv
181 teavnfwqql srprqplllq vsvqrehlgp lasgahklvr fasqgapagl gepqlelhtl
241 dlrdygaqgd cdpeapmteq trccrqemyi dlqqmkwakn wvleppqfla yecvqtcqqp
301 pealafnwpf lqprqciase taslpmivsi keggrtrpqv vslpnmrvqk cscasdgalv
361 prrlqp
```

RXXR cleavage sites are underlined. The cysteine knot domain is double underlined.

Human Lefty-B protein (NCBI RefSeq ID NP_066277) (SEQ ID NO:2):
```
  1 mqplwlcwal wvlplaspga altgeqllgs llrqlqlkev ptldradmee lvipthvraq
 61 yvallqrshg drsrgkrfsq sfrevagrfl aleasthllv fgmeqrlppn selvqavlrl
121 fqepvpkaal hrhqrlsprs ararvtvewl rvrddgsnrt slidsrlvsv hesgwkafdv
181 teavnfwqql srprqplllq vsvqrehlgp lasgahklvr fasqgapagl gepqlelhtl
241 dlgdygaqgd cdpeapmteq trccrqemyi dlqqmkwaen wvleppqfla yecvqtcrqp
301 pealafkwpf lqprqciase tdslpmivsi keggrtrpqv vslpnmrvqk cscasdgalv
361 prrlqp
```

RXXR cleavage sites are underlined. The cysteine knot domain is double underlined.

Murine Lefty-1 cDNA (NCBI RefSeq ID NM_010094) (SEQ ID NO:13):
```
  1 aggacacctc agggacacac acatccaagg ctcctcttcc cggacagcac catgccattc
 61 ctgtggctct gctgggcact ctgggcactg tcgctggtta gcctcaggga agccctgacc
121 ggagagcaga tcctgggcag cctgctgcaa cagctgcagc tcgatcaacc gccagtcctg
181 gacaaggctg atgtggaagg gatggtcatc ccctcgcacg tgaggactca gtatgtggcc
241 ctgctacaac acagccatgc cagccgctcc cgaggcaaga ggttcagcca gaaccttcga
301 gaggtggcag gcaggttcct ggtgtcagag acctccactc acctgctagt gttcggaatg
361 gagcagcggc tgccgcctaa cagcgagctg gtgcaggctg tgctgcggct gttccaggag
421 cctgtgccca acagctctc ccggaggcaa aagaggctgt ccccacacag tgcccgggct
481 cgggtcacca ttgaatggct gcgcttccgc gacgacggcc ccaaccgcac tgcccttatc
```

-continued

```
 541 gattctaggc tcgtgtccat ccacgagagc ggctggaagg ccttcgacgt gaccgaggcc 601 gtgaacttct ggcagcagct gagccggccg aggcagccgc tgctgctcca ggtgtcggtg 661 cagagggagc atctggggcc gggaacctgg agctcacaca agttggttcg tttcgcggcg 721 caggggacgc cggatggcaa ggggcagggc gagccacagc tggagctgca cacgctggac 781 ctcaaggact atggagctca aggcaattgt gaccccgagg caccagtgac tgaaggcacc 841 cgatgctgtc gccaggagat gtacctggac ctgcagggga tgaagtgggc cgagaactgg 901 atcctagaac cgccagggtt cctgacatat gaatgtgtgg gcagctgcct gcagctaccg 961 gagtccctga ccagcaggtg gccatttctg gggcctcggc agtgtgtcgc ctcagagatg 1021 acctccctgc ccatgattgt cagcgtgaag gagggaggca ggaccaggcc tcaagtggtc 1081 agcctgccca acatgagggt gcagaccgtg agctgcgcct cagatggggc gctcataccc 1141 aggaggctgc agccataggc gcggggtgtg gcttccccaa ggatgtgcct ttcatgcaaa 1201 tctgaagtgc tcattatact gggagagctg gggattctaa ctccctaatg gcaatccct 1261 gtgtgtgctc tttgcttcct ctgaagtagc ctcatcccta aattttacc ttcgaggaat 1321 gtgactcgct ggcccctgga ggcgctctga cccagtggtc tctgtccttc atattgttca 1381 ctgcactgta tgcgaagcac ttacatgtat agatactgca aaccaaggac agaatcccca 1441 attgccattg ttcccttaat ttgtcgctga atctgggctg agtcccagtc ttgactctgg 1501 acctaagcca caagttgggc aaacatgtcc aacctaggca atactggctt tgctagatgt 1561 gaataaaata tgctttgttt tgt
```

Murine Lefty-2 cDNA (NCBI RefSeq ID NM_177099) (SEQ ID NO:14):
```
   1 gtcccaagaa cttttcaggg cacttttagg gacgcatata tccacgattc ctcctgggca 61 gcgccatgaa gtccctgtgg ctttgctggg cactctgggt actgcccctg ctggccctg 121 gggcagcgat gaccgaggaa caggtcctga gcagtctact gcagcagctg cagctcagcc 181 aggcccccac cctggacagc gcggatgtgg aggagatggc catccctacc cacgtgaggt 241 cccagtatgt ggccctgctg cagggaagtc acgctgaccg ctcccgaggc aagaggttca 301 gccagaattt tcgagaggtg gcaggcaggt tcctgatgtc agagacctcc actcacctgc 361 tagtgttcgg aatggagcag cggctgccgc ctaacagcga gctggtgcag gctgtgctgc 421 ggctgttcca ggagcctgtg cccagaacag ctctccggag gtttgagagg ctgtccccac 481 acagtgcccg ggctcgggtc accattgaat ggctgagagt ccgtgaggat ggctccaatc 541 gcactgccct catcgactct aggctcgtgt ccatccacga gagcggctgg aaggccttcg 601 acgtgaccga ggccgtgaac ttctggcagc agctgagccg gccgaggcag ccgctgctgc 661 tccaggtgtc ggtgcagagg gagcatctgg ggccggggac ctggagcgca caagttgg 721 tccgtttcgc ggcgcagggg acgccggacg gcaaggggca gggcgagcca cagctggagc 781 tgcacacgct ggacctcaag gactacggag ctcaaggcaa ttgtgacccc gaggtaccag 841 tgactgaagg cacccgatgc tgtcgccagg agatgtacct ggacctgcag gggatgaagt 901 gggccgagaa ctggatccta gaaccgccag ggttcctgac gtatgaatgt gtgggcagct 961 gcctgcagct accagagtcc ctgaccatcg ggtggccatt tctggggcct cggcagtgtg 1021 ttgcctcaga gatgaccctcc ttgcccatga ttgtcagtgt gaaggaggga ggcaggacca 1081 ggcctcaagt ggtcagcctg cccaacatga gggtgcagac ctgtagctgc gcctcagatg 1141 gggcgctcat acccaggggg atagatctgt agtctccctg tccacagatg tattctcagt
```

-continued

```
1201 gagcttgtcc taacttagtg ctctcgtcag acctttgctc tacagtcttg gttttcttgt
1261 ccatcaccca gtttaagcac ttacatgggt aaatcatgtc actccagtag acacactga
1321 ccccacttag ccaaggacat ggctatgcag tgaacaggtt cgcatctgag tctgttttct
1381 ggccagaact cagcttaatg tacaacaaaa ccctacggtg agaacagggg aatcaaaagc
1441 tcgtttactc ttacaccgtg attactggca tcaacgtacc atgtcaggga ctgcccacag
1501 caggctggga gggagacatc tcagaagcct gcggcagctc cttgtgaaaa accgttgttc
1561 ccatttctcc taaccttagc cctagacaag agctgtatag atttcatgtg tgtgactgct
1621 tttcagttgg ccttggtgtt catagttatt ctatattatt tgactttcct actcctttct
1681 ccttctgccc tggtgaattc tatgaaacta gatgttcctt gatgtaatga ttcttaaaca
1741 attaaaaagt tgaggcatgg gacacagcac agcacagtcc tgatggccca ggtgcatgct
1801 gtagatgtat tctgtgtgct cttatcttgg aaacaatgca ataactttgc aatgttagtt
1861 cagattaatg tttgacttgc aaagaaagtt tgaagaaatt attagaaagt gaaatagagc
1921 caacactggg atcccgaaaa gaaaaaagct attgaagtta tgaaataagt tttgcacaaa
1981 atttgagagt gtttcctgga taagcaagta tagaatacat aaaatcttat attagtaaaa
2041 ctaagccaaa acaccgggac tcttaggagg gtcactgcgt gcaatgtgca gaagcagaaa
2101 gctggcagaa ctgccgagtt aagggtgtac ctgagtctttt ctggccattg cctggcagct
2161 ttgcccatgt catttattgt cagagcttca cgggaaaatg caagtagccg acttcggagc
2221 tctgagctct ggagtataat aagtcaaaag gtaaagttta ataatgata agtttgcaat
2281 aattattatt ttggccagag gcctgggaat aggggaagct tgaaactctg ggggaacaat
2341 tataattctt gattctttgt gtgatgtggg tattgttttg aatttgattt ggcaacgatt
2401 atacaatgtc ttttttttcct atctgcattt ggagtatcaa taaaagactg gggcaagaga
2461 aaaaaaaaaa aaaaaaaaaa aaaaaaaaaa aaaaaaaaaa aaaaaaaaaa aaaaaaaaaa
2521 aaaaaaaaaa aaaa
```

Human Lefty-A cDNA (NCBI RefSeq ID NM_003240) (SEQ ID NO:15):
```
   1 acacccagct gcctgagacc ctccttcaac ctccctagag gacagcccca ctctgcctcc
  61 tgctccccca gggcagcacc atgtggcccc tgtggctctg ctgggcactc tgggtgctgc
 121 ccctggctgg ccccggggcg gccctgaccg aggagcagct cctgggcagc ctgctgcggc
 181 agctgcagct cagcgaggtg cccgtactgg acaggggccga catggagaag ctggtcatcc
 241 ccgcccacgt gagggcccag tatgtagtcc tgctgcggcg cagccacggg gaccgctccc
 301 gcggaaagag gttcagccag agcttccgag aggtggccgg caggttcctg cgtcggagg
 361 ccagcacaca cctgctggtg ttcggcatgg agcagcggct gccgcccaac agcgagctgg
 421 tgcaggccgt gctgcggctc ttccaggagc cggtccccaa ggccgcgctg cacaggcacg
 481 ggcggctgtc ccgcgcagc gcccaggccc gggtgaccgt cgagtggctg cgcgtccgcg
 541 acgacggctc caaccgcacc tccctcatcg actccaggct ggtgtccgtc cacgagagcg
 601 gctggaaggc cttcgacgtg accgaggccg tgaacttctg gcagcagctg agccggcccc
 661 ggcagccgct gctgctacag gtgtcggtgc agagggagca tctgggcccg ctggcgtccg
 721 gcgcccacaa gctggtccgc tttgcctcgc aggggcgcc agccgggctt ggggagcccc
 781 agctggagct gcacaccctg gacctccagg actatggagc tcagggcgac tgtgaccctg
 841 aagcaccaat gaccgagggc acccgctgct gccgccagga gatgtacatt gacctgcagg
```

-continued

```
 901 ggatgaagtg ggccaagaac tgggtgctgg agccccggg cttcctggct tacgagtgtg
 961 tgggcacctg ccagcagccc ccggaggccc tggccttcaa ttggccattt ctggggccgc
1021 gacagtgtat cgcctcggag actgcctcgc tgcccatgat cgtcagcatc aaggagggag
1081 gcaggaccag gccccaggtg gtcagcctgc caacatgag ggtgcagaag tgcagctgtg
1141 cctcggatgg ggcgctcgtg ccaaggaggc tccagccata ggcgcctggt gtatccattg
1201 agccctctaa ctgaacgtgt gcatagaggt ggtcttaatg taggtcttaa ctttatactt
1261 agcaagttac tccatcccaa tttagtgctc ctgtgtgacc ttcgccctgt gtccttccat
1321 ttcctgtctt tcccgtccat cacccatcct aagcacttac gtgagtaaat aatgcagctc
1381 agatgctgag ctctagtagg aaatgctggc atgctgatta caagatacag ctgagcaatg
1441 cacacatttt cagctgggag tttctgttct ctggcaaatt cttcactgag tctgaacaa
1501 taatacccta tgattagaac tggggaaaca gaactgaatt gctgtgttat atgaggaatt
1561 aaaaccttca aatctctatt tcccccaaat actgacccat tctggacttt tgtaaacata
1621 cctaggcccc tgttcccctg agagggtgct aagaggaagg atgaagggct tcaggctggg
1681 ggcagtggac agggaattgg gatacctgga ttctggttct gacagggcca caagctagga
1741 tctctaacaa acgcagaagg ctttggctcg tcatttcctc ttaaaaagga ggagctgggc
1801 ttcagctcta gaacttcat tgccctgggg atcagacagc ccctacctac ccctgcccac
1861 tcctctggag actgagcctt gcccgtgcat atttaggtca tttcccacac tgtcttagag
1921 aacttgtcac cagaaaccac atgtatttgc atgttttttg ttaatttagc taaagcaatt
1981 gaatgtagat actcagaaga aataaaaaat gatgtttcaa aaaaaaaaa aaaaaaaaa
2041 aaaaaaaaa aaaaaaaaa aaaaaaaaa aaaaaaaaa aaaaaaaaa aaaaaaaaa
2101 aa
```

Human Lefty-B cDNA (NCBI RefSeq ID NM_020997) (SEQ ID NO:16):

```
   1 gcctgagacc ctcctgcagc cttctcaagg gacagcccca ctctgcctct tgctcctcca
  61 gggcagcacc atgcagcccc tgtggctctg ctgggcactc tgggtgttgc ccctggccag
 121 ccccggggcc gccctgaccg gggagcagct cctgggcagc ctgctgcggc agctgcagct
 181 caaagaggtg cccaccctgg acagggccga catggaggag ctggtcatcc ccacccacgt
 241 gagggcccag tacgtggccc tgctgcagcg cagccacggg gaccgctccc gcggaaagag
 301 gttcagccag agcttccgag aggtggccgg caggttcctg gcgttggagg ccagcacaca
 361 cctgctggtg ttcggcatgg agcagcggct gccgcccaac agcgagctgg tgcaggccgt
 421 gctgcggctc ttccaggagc cggtccccaa ggccgcgctg cacaggcacg gcggctgtc
 481 cccgcgcagc gcccgggccc gggtgaccgt cgagtggctg cgcgtccgcg acgacggctc
 541 caaccgcacc tccctcatcg actccaggct ggtgtccgtc cacagagcg ctggaaggc
 601 cttcgacgtg accgaggccg tgaacttctg gcagcagctg agccggcccc ggcagccgct
 661 gctgctacag gtgtcggtgc agagggagca tctgggcccg ctggcgtccg cgcccacaa
 721 gctggtccgc tttgcctcgc agggggcgcc agccgggctt ggggagcccc agctggagct
 781 gcacaccctg gaccttgggg actatggagc tcagggcgac tgtgaccctg aagcaccaat
 841 gaccgagggc acccgctgct gccgccagga gatgtacatt gacctgcagg ggatgaagtg
 901 ggccgagaac tgggtgctgg agccccggg cttcctggct tatgagtgtg tgggcacctg
 961 ccggcagccc ccggaggccc tggccttcaa gtggccgttt ctggggcctc gacagtgcat
```

```
-continued
1021 cgcctcggag actgactcgc tgcccatgat cgtcagcatc aaggagggag gcaggaccag 1081 gccccaggtg gtcagcctgc ccaacatgag ggtgcagaag tgcagctgtg cctcggatgg 1141 tgcgctcgtg ccaaggaggc tccagccata ggcgcctagt gtagccatcg agggacttga 1201 cttgtgtgtg tttctgaagt gttcgagggt accaggagag ctggcgatga ctgaactgct 1261 gatggacaaa tgctctgtgc tctctagtga gccctgaatt tgcttcctct gacaagttac 1321 ctcacctaat ttttgcttct caggaatgag aatctttggc cactggagag cccttgctca 1381 gttttctcta ttcttattat tcactgcact atattctaag cacttacatg tggagatact 1441 gtaacctgag ggcagaaagc ccaatgtgtc attgtttact tgtcctgtca ctggatctgg 1501 gctaaagtcc tccaccacca ctctggacct aagacctggg gttaagtgtg ggttgtgcat 1561 ccccaatcca gataataaag actttgtaaa acatgaataa aacacatttt attctaaaaa 1621 aaaaaaaaaa aaaaaaaaaa aaaaaaa
```

It is expected that Lefty proteins also exist in other species, including all mammals.

Unless specifically stated otherwise, "Lefty polypeptide" includes both wild-type (including naturally occurring alleles) and altered ("derivative") Lefty forms, including various truncated and variant versions of Lefty that retain the ability to inhibit the activity of a TGF-β family member such as Nodal, myostatin or GDF-11.

As used herein, the term "Lefty activity" refers to one or more of the activities which are exhibited by the Lefty proteins of the present disclosure. In particular, "Lefty activity" includes the ability to bind to one or more of Nodal, myostatin and GDF-11.

"Specifically binds" includes reference to the preferential association of a ligand, in whole or part, with a particular target molecule (i.e., "binding partner" or "binding moiety") relative to compositions lacking that target molecule. It is, of course, recognized that a certain degree of non-specific interaction may occur between the subject Lefty polypeptides and other non-target proteins. Typically specific binding results in a much stronger association between the Lefty polypeptide and the target protein (e.g., Nodal, myostatin and/or GDF-11) than between the Lefty polypeptide and other proteins.

2. Lefty Derivatives

The disclosure provides novel derivatives of Lefty proteins. The term "Lefty derivatives" includes altered forms of known Lefty proteins, such as variants induced by mutagenesis, insertions or deletions, and fragments of Lefty proteins, which variants retain Nodal, myostatin and/or GDF-11 binding activity. Lefty derivatives also include proteins sharing structural and/or functional similarity to known Lefty proteins, including those proteins which are described further herein. Such proteins may have amino acid sequences sharing significant sequence identity (e.g., at least about 50%, 60%, 70%, 80%, 90%, 95%, 99% or more) with the human or mouse Lefty proteins, over the full-length, the mature portion, or at least within the Regions 2 and 4 of the human or mouse Lefty. Lefty derivatives also include proteins that have amino acid sequences that are encoded by nucleic acid sequences that hybridize under stringent conditions with the coding sequences for human or mouse Lefty, particularly that portion of the coding sequence for the mature portion, especially Regions 2 and 4. The term "Lefty derivative" excludes any of SEQ ID Nos. 1-4.

As described in FIGS. 1-5, Lefty proteins may be divided into portions, including a signal sequence, a propeptide, and a mature portion. The mature portion can be viewed as having five regions. Region 1 is the portion of the mature polypeptide that is N-terminal to C1 (the first cysteine of the cystine knot domain). Regions 2 and 4 correspond to Loops A and B and participate in ligand binding (ligands such as Nodal, myostatin and GDF-11). Region 3 of Lefty proteins lacks the alpha helix and the cysteine that participates in intermolecular crosslinking. Region 5 is the portion that is C-terminal to the final cysteine of the cystine knot domain. The propeptide will be long or short, depending on whether the upstream (N-terminal) or downstream RXXR cleavage site is used. Conversely, the mature portion, if expressed with a propeptide, will be short or long, depending on which RXXR cleavage site is used.

It is expected that Regions 2 and 4 mediate binding to Nodal, myostatin and GDF-11, and accordingly, any of Regions 1, 3 and 5 may be altered, in so far as ligand binding is retained. It is expected that the basic cystine knot structure will generally be conserved in Lefty derivatives that retain ligand binding activity.

Lefty proteins from other species, especially those of mammals, can be readily obtained by standard molecular biology protocols, such as PCR, low stringency hybridization, or antibody-mediated screening of expression libraries using antibodies cross-reacting with identified Lefty homologs in target species.

In certain embodiments, isolated fragments of the Lefty polypeptides can be obtained by screening polypeptides recombinantly produced from the corresponding fragment of the nucleic acid encoding a Lefty polypeptide (e.g., SEQ ID Nos: 13-16). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function to bind to Nodal, myostatin and/or GDF-11, or for a cell-based activity, such as stimulation of muscle growth.

In certain embodiments, a Lefty derivative has an amino acid sequence that is at least 75% identical to an amino acid sequence as set forth in any of SEQ ID Nos. 1-4, 9, 10, 11, 12 or 22. In certain cases, the Lefty derivative has an amino acid sequence at least 80%, 85%, 90%, 95%, 97%, 98%, 99% or 100% identical to an amino acid sequence as set forth in any of SEQ ID Nos. 14, 9, 10, 11, 12 or 22. Preferably such variants retain the ability to bind to Nodal, myostatin and/or GDF-11.

In certain embodiments, the present invention contemplates making functional Lefty derivatives by modifying the structure of a Lefty polypeptide. Such modifications may be made, for example, for such purposes as enhancing therapeutic efficacy, or stability (e.g., ex vivo shelf life and resistance to proteolytic degradation in vivo). Lefty derivatives can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a Lefty derivative results in a functional homolog can be readily determined by assessing the ability of the variant propeptide to produce a response in cells, or to bind to ligand, in a fashion similar to the wild-type Lefty.

In certain embodiments, the present invention contemplates making mutations in a proteolytic cleavage site of a Lefty sequence to make the site less susceptible to proteolytic cleavage. Computer analysis (using a commercially available software, e.g., MacVector, Omega, PCGene, Molecular Simulation, Inc.) can be used to identify proteolytic cleavage sites. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the Lefty sequences so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which are specifically recognized by appropriate cellular glycosylation enzymes. The alteration may also be made by the addition of, or substitution by, one or more serine or threonine residues to the sequence of the wild-type Lefty (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a Lefty polypeptide is by chemical or enzymatic coupling of glycosides to the Lefty polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a Lefty polypeptide may be accomplished chemically and/or enzymatically. Chemical deglycosylation may involve, for example, exposure of the Lefty polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118: 131. Enzymatic cleavage of carbohydrate moieties on Lefty polypeptide can be achieved by the use of a variety of endo- and exo-glycosidases as described by Thotakura et al. (1987) Meth. Enzymol. 138:350. The nucleic acid and/or amino acid sequence of a propeptide may be adjusted, as appropriate, depending on the type of expression system used, as mammalian, yeast, insect and plant cells may all introduce differing glycosylation patterns that can be affected by the amino acid sequence of the peptide.

Examples of sequence modifications that can be made in Lefty-A are set forth below:

```
                                            (SEQ ID NO:28)
LTEEQLLGSLLRQLQLSEVPVLDRADMEKLVIPAHVRAQYVVLLRRSHGD

RSRGKRFSQSFREVAGRFLASEASTHLLVFGMEQRLPPNSELVQAVLRLF

QEPVPKAAL(N)HR(T/G)HGR(N)LSPRSAQARVTVEWLRVRDDGSNRT

SLIDSRLVSVHESGWKAFDVTEAVNFWQQLSRPRQPLLLQVSVQREHLGP

LASGAHKLVRFASQGAPAGLGEPQLELHTLDLRDYGAQGDCDPEAP(N)M

TE(N)GTRCCRQEMYIDLQGMKWAKNWVLEPPGFLAYECVGTCQQPPEA(

N)LA(T)FNW(S)P(T)FLGPRQCIASETASLPMIVSIKEGGRTRPQVVS

LPNMRVQKCSCASDGALVPRRLQP
```

The first and second cleavage sites are underlined. Possible alterations, which may be used together, individually, or in combinations, are shown in brackets following the amino acid that would be altered. In this version, the polypeptide will be cleaved at the first site to give rise to a 34 kDa Lefty-A polypeptide beginning with the bold font pheylalanine (F). The second RXXR cleavage site may be altered to eliminate cleavage (e.g., R→G change) or to eliminate cleavage and introduce a glycosylation site (other changes shown). Other mutations are shown to introduce glycosylation sites at the C-terminal end of Region 1 and in Region 3. Similar mutations may be made in any of SEQ ID Nos. 2-4.

This disclosure contemplates methods of generating mutants, including sets of combinatorial mutants of Lefty polypeptides, as well as truncation mutants; pools of combinatorial mutants are especially useful for identifying functional variant sequences. The purpose of screening such combinatorial libraries may be to generate, for example, Lefty derivatives which can act as antagonists of Nodal, myostatin and/or GDF-11. For example, a Lefty polypeptide variant may be screened for ability to bind to a Nodal, myostatin and/or GDF-11 polypeptide, or for the ability to prevent binding of a Nodal, myostatin and/or GDF-11 to a cell expressing a receptor, such as an ActRIIA or B. The activity of a Lefty polypeptide variant may also be tested in a cell-based or in vivo assay. For example, the effect of a Lefty polypeptide variant on the expression of genes involved in muscle cell growth or myostatin-sensitive promoter may be assessed. Likewise, a Lefty polypeptide may be administered to a mouse or other animal, and one or more bone properties, such as density or volume may be assessed. The healing rate for bone fractures may also be evaluated. The effect of a Lefty polypeptide on gene expression changes caused by any of myostatin, Nodal or GDF-11 may be assessed. For example, an A-204 reporter gene assay may be used to evaluate the effects of Lefty polypeptides on signaling by GDF-11 and myostatin or other TGF-beta family members. A cell line, (e.g., human rhabdomyosarcoma cell line) may be transfected with a reporter vector that places a reporter gene (e.g., luciferase) under direction of a TGF-beta signaling-sensitive regulatory element (e.g., pGL3(CAGA)12 described in Dennler et al, 1998, EMBO 17: 3091-3100.) The CAGA12 motif is present in TGF-Beta responsive genes (PAI-1 gene), and this type of vector is of general use for factors signaling through Smad2 and 3. Lefty polypeptides may be tested for effects on the reporter gene activity.

Combinatorially-derived variants can be generated which have a selective potency relative to a naturally occurring Lefty polypeptide. Likewise, mutagenesis can give rise to variants which have intracellular half-lives dramatically different than the corresponding wild-type propeptide. For example, the altered protein can be rendered either more stable or less stable to proteolytic degradation.

A combinatorial library may be produced by way of a degenerate library of genes encoding a library of polypeptides which each include at least a portion of potential Lefty polypeptide sequences. For instance, a mixture of synthetic oligonucleotides can be enzymatically ligated into gene sequences such that the degenerate set of potential Lefty polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, Lefty polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of Lefty polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of Lefty polypeptides. The most widely used technique for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

In certain embodiments, the Lefty polypeptides of the present invention include peptidomimetics. As used herein, the term "peptidomimetic" includes chemically modified peptides and peptide-like molecules that contain non-naturally occurring amino acids, peptoids, and the like. Peptidomimetics provide various advantages over a peptide, including enhanced stability when administered to a subject. Methods for identifying a peptidomimetic are well known in the art and include the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). Where no crystal structure of a target molecule is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of the Lefty polypeptides. For instance, non-hydrolyzable peptide analogs of such residues can be generated using benzodiazepine (e.g., see Freidinger et al., in Peptides: Chemistry and Biology, G. R. Marshall ed., ESCOM Publisher: Leiden, Netherlands, 1988), azepine (e.g., see Huffman et al., in Peptides: Chemistry and Biology, G. R. Marshall ed., ESCOM Publisher: Leiden, Netherlands, 1988), substituted gamma lactam rings (Garvey et al., in Peptides: Chemistry and Biology, G. R. Marshall ed., ESCOM Publisher: Leiden, Netherlands, 1988), keto-methylene pseudopeptides (Ewenson et al., 1986) J. Med. Chem. 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., (1985) Tetrahedron Lett 26:647; and Sato et al., (1986) J Chem Soc Perkin Trans 1:1231), and b-aminoalcohols (Gordon et al., (1985) Biochem Biophys Res Commun 126:419; and Dann et al., (1986) Biochem Biophys Res Commun 134:71).

In certain embodiments, the Lefty polypeptides of the invention may further comprise post-translational modifications in addition to any that are naturally present in the propeptide. Such modifications include, but are not limited to, acetylation, carboxylation, glycosylation, phosphorylation, lipidation, and acylation. As a result, the modified Lefty polypeptides may contain non-amino acid elements, such as polyoxyalkylene glycols (e.g., polyethylene glycols, polypropylene glycols), lipids, poly- or mono-saccharide, and phosphates. Effects of such non-amino acid elements on the functionality of a Lefty polypeptide may be tested as described herein. When a Lefty polypeptide is produced in cells by cleaving a nascent form of the Lefty polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the Lefty polypeptide.

The various Lefty polypeptides may be prepared as fusion proteins. A fusion protein may include one or more additional polypeptide portion that enhance one or more of in vivo stability, in vivo half life, uptake/administration, tissue localization or distribution, formation of protein complexes, and/or purification. For example, a fusion protein may include an immunoglobulin Fc domain and/or a purification subsequence selected from: an epitope tag, a FLAG tag, a polyhistidine sequence, and a GST fusion. A Lefty polypeptide may include one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

A fusion protein or coupled protein system (e.g. non-fusion covalent linkage by crosslinking) may also include a second antagonist domain, which is a polypeptide affinity reagent that selectively binds to Nodal, myostatin and/or GDF-11 and competes with the binding of an ALK7 or ALK4 receptor. The affinity reagent may be an antibody agent. An antibody agent may be, for example, a recombinant antibody; a monoclonal antibody; a VH domain; a VL domain; an scFv; an Fab fragment; an Fab' fragment; an F(ab')2; an Fv; or a disulfide linked Fv, a fully human antibody or a humanized chimeric antibody, or an antigen binding fragment thereof. An affinity reagent is a peptide or scaffolded peptide that selectively binds to Nodal, myostatin and/or Lefty and competes with the binding of an ALK7 or ALK4 receptor. An affinity reagent may include a Nodal, myostatin and/or GDF-11 binding domain of ALK7 or ALK4. For example, an extracellular domain of ALK7 or ALK4 (preferably human ALK7 or ALK4) may be used. The affinity reagent may be a small organic molecule that selectively binds to Nodal, myostatin and/or GDF-11 and competes with the binding of an ALK7 or ALK4 receptor.

An example of a human ALK7 ligand binding domain is shown below:

(SEQ ID NO:26)
LKCVCLLCDSSNFTCQTEGACWASVMLTNGKEQVIKSCVSLPELNAQVFC

HSSNNVTKTECCFTDFCNNITLHLP

An example of a human ALK4 myostatin binding domain is shown below:

(SEQ ID NO:27)
ALLCACTSCLQANYTCETDGACMVSIFNLDGMEHHVRTCIPKVELVPAGK

PFYCLSSEDLRNTHCCYTDY

It is understood that different elements of the fusion proteins may be arranged in any manner that is consistent with the desired functionality. For example, a Lefty polypeptide may be placed C-terminal to a heterologous domain, or, alternatively, a heterologous domain may be placed C-terminal to a Lefty polypeptide. The propeptide domain and the heterologous domain need not be adjacent in a fusion protein, and additional domains or amino acid sequences may be included C- or N-terminal to either domain or between the domains.

In certain embodiments, the Lefty polypeptides of the present invention contain one or more modifications that are capable of stabilizing the Lefty polypeptides. For example, such modifications may enhance the in vitro half life of the propeptides, enhance circulatory half life of the propeptides or reducing proteolytic degradation of the propeptides. Such stabilizing modifications include, but are not limited to, fusion proteins (including, for example, fusion proteins comprising a Lefty polypeptide and a stabilizer domain), modifications of a glycosylation site (including, for example, addition of a glycosylation site to a Lefty polypeptide), and modifications of carbohydrate moiety (including, for example, removal of carbohydrate moieties from a Lefty polypeptide). In the case of fusion proteins, a Lefty polypeptide is fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a carbohydrate moiety, or nonproteinaceous polymer, such as polyethylene glycol (PEG). PEG may be affixed to Lefty polypeptides in a variety of sizes, ranging from 1000 D to 50,000 D or more molecular weight polymers. PEG polymers may be affixed to propeptides in a selective, residue specific manner, particularly when directed against the N-terminal amine or an engineered cysteine. PEG polymers may also be affixed in a relatively uncontrolled reaction, in which primary amines and/or sulfhydryl groups may be reacted. The stoichiometry may range from 1:1 (PEG:peptide) to 2:1 and higher.

In certain embodiments, the Lefty polypeptide is fused with an immunoglobulin Fc domain. In a preferred embodiment, the Fc domain is an IgG1 Fc fragment. An IgG1 Fc fragment may include various alterations, including, for example, mutations that reduce binding to Fcγ Receptor and mutations that decreased binding to MHC class I-related Fc-receptor (FcRN). Examples of mutations include mutations in the an Fc portion at positions 265 (Asp to Ala), 322 (Lys to Ala), and 434 (Asn to Ala).

In certain embodiments, the present invention makes available isolated and/or purified forms of the Lefty polypeptides, which are isolated from, or otherwise substantially free of, other proteins.

In certain embodiments, Lefty polypeptides (unmodified or modified) of the invention can be produced by a variety of art-recognized techniques. For example, such Lefty polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the Lefty polypeptides, fragments or variants thereof may be recombinantly produced using various expression systems (e.g., E. coli, Chinese Hamster Ovary cells, COS cells, baculovirus) as is well known in the art (also see below). In a further embodiment, the modified or unmodified Lefty polypeptides may be produced by digestion of naturally occurring or recombinantly produced Lefty polypeptide by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites.

3. Nucleic Acids Encoding Lefty Polypeptides

In certain aspects, the invention provides isolated and/or recombinant nucleic acids encoding any of the Lefty polypeptides, including derivatives, disclosed herein. The subject nucleic acids may be single-stranded or double stranded. Such nucleic acids may be DNA or RNA molecules. These nucleic acids are may be used, for example, in methods for making Lefty polypeptides or as direct therapeutic agents (e.g., in a gene therapy approach).

In other embodiments, nucleic acids of the invention also include nucleotide sequences that hybridize under highly stringent conditions to the nucleotide sequence designated in SEQ ID Nos: 13-16, complement sequence of SEQ ID Nos: 13-16, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID Nos: 13-16 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding a Lefty polypeptide and operably linked to at least one regulatory sequence. Regulatory sequences are art-recognized and are selected to direct expression of the Lefty polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a Lefty polypeptide. Such useful expression control sequences, include, for example, the CMV promoter, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant Lefty polypeptides include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREPderived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant SLC5A8 polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a particular embodiment, a vector will be designed for production of a subject Lefty polypeptide in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject Lefty polypeptides in cells propagated in culture, e.g., to produce proteins, including fusion proteins or variant proteins, for purification.

This invention also pertains to a host cell transfected with a recombinant gene including a coding sequence for one or more of the subject Lefty polypeptides. The host cell may be any prokaryotic or eukaryotic cell. For example, a Lefty polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject Lefty polypeptides. For example, a host cell transfected with an expression vector encoding a Lefty polypeptide can be cultured under appropriate conditions to allow expression of the Lefty polypeptide to occur. The Lefty polypeptide may be secreted and isolated from a mixture of cells and medium containing the propeptide. Alternatively, the polypeptide may be retained cytoplasmically or in a membrane fraction and the cells harvested, lysed and the protein isolated. A cell culture includes host cells, media and other byproducts. Suitable media for cell culture are well known in the art. The polypeptide can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the Lefty polypeptide. In a preferred embodiment, the Lefty polypeptide is a fusion protein containing a domain which facilitates its purification (purification domain). For example, a fusion gene coding for a purification leader sequence or C-terminal tail, such as a poly-(His)/enterokinase cleavage site sequence at the N-terminus of the desired portion of the recombinant Lefty polypeptide, can allow purification of the expressed fusion protein by affinity chromatography using a $Ni^{2+}$ metal resin. The purification sequence can then be subsequently removed by treatment with enterokinase to provide the purified Lefty polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Exemplary Therapeutic Uses

The subject Lefty polypeptides, such as the full-length and the N-terminally truncated Lefty derivatives, can be used in a number of therapeutic settings to treat a number of diseases resulting from or exacerbated by the presence of myostatin, Nodal or GDF-11.

In certain embodiments, the subject Lefty polypeptides are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject myostatin include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

In DMD, boys begin to show signs of muscle weakness as early as age 3. The disease gradually weakens the skeletal or voluntary muscles, those in the arms, legs and trunk. By the early teens or even earlier, the boy's heart and respiratory muscles may also be affected. BMD is a much milder version of DMD. Its onset is usually in the teens or early adulthood, and the course is slower and far less predictable than that of DMD. (Though DMD and BMD affect boys almost exclusively, in rare cases they can affect girls.

Until the 1980s, little was known about the cause of any kind of muscular dystrophy. In 1986, the dystrophin gene deficiency was identified as the cause of DMD. BMD results from different mutations in the same gene. BMD patients have some dystrophin, but it's either insufficient in quantity or poor in quality. Having some dystrophin protects the muscles of those with BMD from degenerating as badly or as quickly as those of people with DMD.

Recent results demonstrate that blocking or eliminating Myostatin function in vivo can effectively treat at least certain symptoms in DMD and BMD patients (Bogdanovich et al., supra; Wagner et al., supra). Thus, the subject Lefty derivatives, especially the N-terminally truncated versions thereof, constitute an alternative means of blocking the function of myostatin in vivo in DMD and BMD patients.

Similarly, the subject Lefty derivatives, especially the N-terminally truncated versions thereof, provide an effective means to increase muscle mass in other disease conditions that are in need of muscle growth. For example, Gonzalez-Cadavid et al. (supra) reported that that myostatin expression correlates inversely with fat-free mass in humans and that increased expression of the myostatin gene is associated with weight loss in men with AIDS wasting syndrome. By inhibiting the function of myostatin in AIDS patients, at least certain symptoms of AIDS may be alleviated, if not completely eliminated, thus significantly improving quality of life in AIDS patients.

Since loss of myostatin function is also associated with fat loss without diminution of nutrient intake (Zimmers et al., supra; McPherron and Lee, supra), the subject Lefty derivatives, especially the N-terminally truncated versions thereof, may further be used as a therapeutic agent for slowing or preventing the development of obesity and type II diabetes. It should also be noted that Lefty derivatives may affect obesity for reasons unrelated to myostatin.

The cancer anorexia-cachexia syndrome is among the most debilitating and life-threatening aspects of cancer. Progressive weight loss in cancer anorexia-cachexia syndrome is a common feature of many types of cancer and is responsible not only for a poor quality of life and poor response to chemotherapy, but also a shorter survival time than is found in patients with comparable tumors without weight loss. Associated with anorexia, fat and muscle tissue wasting, psychological distress, and a lower quality of life, cachexia arises from a complex interaction between the cancer and the host. It is one of the most common causes of death among cancer patients and is present in 80% at death. It is a complex example of metabolic chaos effecting protein, carbohydrate, and fat metabolism. Tumors produce both direct and indirect abnormalities, resulting in anorexia and weight loss. Currently, there is no treatment to control or reverse the process.

Cancer anorexia-cachexia syndrome affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Cachexia should be suspected in patients with cancer if an involuntary weight loss of greater than five percent of premorbid weight occurs within a six-month period.

Since systemic overexpression of myostatin in adult mice was found to induce profound muscle and fat loss analogous to that seen in human cachexia syndromes (Zimmers et al., supra), the subject Lefty derivatives, especially the N-terminally truncated versions thereof as a pharmaceutical composition can be beneficially used as a Myostatin antagonist/blocker to prevent, treat, or alleviate the symptoms of the cachexia syndrome, where muscle growth is desired.

In certain embodiments, the subject Lefty polypeptides can be used to form pharmaceutical compositions that can be beneficially used to prevent, treat, or alleviate symptoms of a host of diseases involving neurodegeneration. The subject Lefty polypeptide as a pharmaceutical composition can be beneficially used to prevent, treat, or alleviate symptoms of diseases with neurodegeneration, including Alzheimer's Disease (AD), Parkinson's Disease (PD), Amyotrophic Lateral Sclerosis (ALS), Huntington's disease, etc.

Alzheimer's disease (AD) is a chronic, incurable, and unstoppable central nervous system (CNS) disorder that occurs gradually, resulting in memory loss, unusual behavior, personality changes, and a decline in thinking abilities. These losses are related to the death of specific types of brain cells and the breakdown of connections between them.

AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses. AD patients most commonly die from pneumonia, 8 to 20 years from disease onset.

Parkinson's disease (PD) is a chronic, incurable, and unstoppable CNS disorder that occurs gradually and results in uncontrolled body movements, rigidity, tremor, and gait difficulties. These motor system problems are related to the death of brain cells in an area of the brain that produces dopamine—a chemical that helps control muscle activity.

In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden. People with PD usually die from pneumonia.

Amyotrophic lateral sclerosis (ALS; Lou Gehrig's disease; motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles.

Most people who have ALS are between 40 and 70 years old. The first motor neurons that weaken are those leading to the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed. Most ALS patients die from respiratory failure or from complications of ventilator assistance like pneumonia, 3-5 years from disease onset. Because ALS symptomology relates to a loss of muscle function, treatments that enhance muscle fiber growth or retention, such as anti-myostatin treatments, may be effective.

The causes of these neurological diseases has remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

Huntington's disease (HD) is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing. The rate of disease progression and the age of onset vary from person to person.

Tay-Sachs disease and Sandhoff disease are glycolipid storage diseases caused by the lack of lysosomal β-hexosaminidase (Gravel et al., in *The Metabolic Basis of Inherited Disease*, eds. Scriver et al., McGraw-Hill, New York, pp. 2839-2879, 1995). In both disorders, $G_{M2}$ ganglioside and related glycolipidssubstrates for β-hexosaminidaseaccumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., *Hum. Mol. Genet.* 6: 1879-1885, 1997).

It is well-known that apoptosis plays a role in AIDS pathogenesis in the immune system. However, HIV-1 also induces neurological disease. Shi et al. (*J. Clin. Invest.* 98: 1979-1990, 1996) examined apoptosis induced by HIV-1 infection of the central nervous system (CNS) in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

Neuronal loss is a also a salient feature of prion diseases, such as Creutzfeldt-Jakob disease in human, BSE in cattle (mad cow disease), Scrapie Disease in sheep and goats, and feline spongiform encephalopathy (FSE) in cats.

The subject Lefty polypeptides are also useful to prevent, treat, and alleviate symptoms of various PNS disorders, such as the ones described below. The PNS is composed of the nerves that lead to or branch off from the CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term peripheral neuropathy encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium *Mycobacterium leprae*, which attacks the peripheral nerves of affected people. According to statistics gathered by the World Health Organization, an estimated 1.15 million people have leprosy worldwide.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic—no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including *Campylobacter jejuni* and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the peripheral nervous system (PNS) and the central nervous system (CNS), as well as other body tissues.

Other PNS diseases treatable with the subject Lefty derivatives, especially the N-terminally truncated Lefty derivatives include: Brachial Plexus Neuropathies (Diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, 6th ed, pp 1351-2); Diabetic Neuropathies (Peripheral, autonomic, and cranial nerve disorders that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy. See Adams et al., Principles of Neurology, 6th ed, p1325); Mononeuropathies (Disease or trauma involving a single peripheral nerve in isolation, or out of proportion to evidence of diffuse peripheral nerve dysfunction. Mononeuropathy multiplex refers to a condition characterized by multiple isolated nerve injuries. Mononeuropathies may result from a wide variety of causes, including ischemia; traumatic injury; compression; connective tissue diseases; cumulative trauma disorders; and other conditions); Neuralgia (Intense or aching pain that occurs along the course or distribution of a peripheral or cranial nerve); Peripheral Nervous System Neoplasms (Neoplasms which arise from peripheral nerve tissue. This includes neurofibromas; Schwannomas; granular cell tumors; and malignant peripheral nerve sheath tumors. See DeVita Jr et al., Cancer: Principles and Practice of Oncology, $5^{th}$ ed, pp 1750-1); Nerve Compression Syndromes (Mechanical compression of nerves or nerve roots from internal or external causes. These may result in a conduction block to nerve impulses, due to, for example, myelin sheath dysfunction, or axonal loss. The nerve and nerve sheath injuries may be caused by ischemia; inflammation; or a direct mechanical effect); Neuritis (A general term indicating inflammation of a peripheral or cranial nerve. Clinical manifestation may include pain; paresthesias; paresis; or hyperthesia); Polyneuropathies (Diseases of multiple peripheral nerves. The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance).

Myostatin inhibitors may also promote bone growth and a combination of bone and muscle strengthening, making the Lefty polypeptides disclosed herein useful for treating disorders such as osteoporosis, frailty, low bone density and tumor induced bone loss.

While the above description provides likely mechanisms of action by which Lefty polypeptides, including Lefty derivatives, may achieve desirable therapeutic effects, such effects may also result from alternative mechanisms or several different mechanisms. It is quite likely that Lefty polypeptides will inhibit additional members of the TGF-beta family, and accordingly, such activity may contribute to a therapeutic effect.

5. Exemplary Formulations

The subject compositions may be used alone, or as part of a conjoint therapy with other compounds/pharmaceutical compositions. In certain embodiments, a pharmaceutical preparation comprising a Lefty polypeptide will be in compliance with guidelines established by the relevant regulatory agency (e.g., the Food and Drug Administration in the U.S.). Such a preparation will typically be substantially pyrogen-free.

The Lefty polypeptides for use in the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the phosphopeptide therapeutics, its use in the pharmaceutical preparation of the disclosure is contemplated. Suitable vehicles and their formulation inclusive of other proteins are described, for example, in the book *Remington's Pharmaceutical Sciences* (*Remington's Pharmaceutical Sciences*. Mack Publishing Co., Easton, Pa., USA 1985). These vehicles include injectable "deposit formulations."

Pharmaceutical formulations of the present disclosure can also include veterinary compositions, e.g., pharmaceutical preparations of the Lefty therapeutics suitable for veterinary uses, e.g., for the treatment of live stock (cow, sheep, goat, pig, and horse, etc.) or domestic animals, e.g., cats and dogs.

Methods of disclosure may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a therapeutic at a particular target site.

The pharmaceutical compositions according to the present disclosure may be administered as either a single dose or in multiple doses. The pharmaceutical compositions of the present disclosure may be administered either as individual therapeutic agents or in combination with other therapeutic agents. The treatments of the present disclosure may be combined with conventional therapies, which may be administered sequentially or simultaneously. The pharmaceutical compositions of the present disclosure may be administered by any means that enables the Lefty polypeptides to reach the targeted cells/tissues/organs. In some embodiments, routes of administration include those selected from the group consisting of oral, intravesically, intravenous, intraarterial, intraperitoneal, local administration into the blood supply of the organ in which the targeted cells reside or directly into the cells. Intravenous administration is the preferred mode of administration. It may be accomplished with the aid of an infusion pump.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, intravesically, nasally, as by, for example, a spray, rectally, intravaginally, parenterally, intracisternally and topically, as by powders, ointments or drops, including buccally and sublingually.

Regardless of the route of administration selected, the compounds of the present disclosure, which may be used in a suitable hydrated form, and/or the pharmaceutical compositions of the present disclosure, are formulated into pharmaceutically acceptable dosage forms such as described below or by other conventional methods known to those of skill in the art.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion of the particular compound being employed, the duration of the treatment, other drugs, compounds and/or materials used in combination with the particular phosphopeptide therapeutic employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above. Generally, intravenous, intracerebroventitricular and subcutaneous doses of the compounds of this disclosure for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other non-human mammals such as equines, cattle, swine and sheep; and poultry and pets in general.

The compound of the disclosure can be administered as such or in admixtures with pharmaceutically acceptable carriers and can also be administered in conjunction with other antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely eliminated when the subsequent is administered.

Generally, the nomenclature used herein and the laboratory procedures utilized in the present disclosure include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8$^{th}$ Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Construction, Expression, and Purification of Lefty Polypeptides

Figure 6:
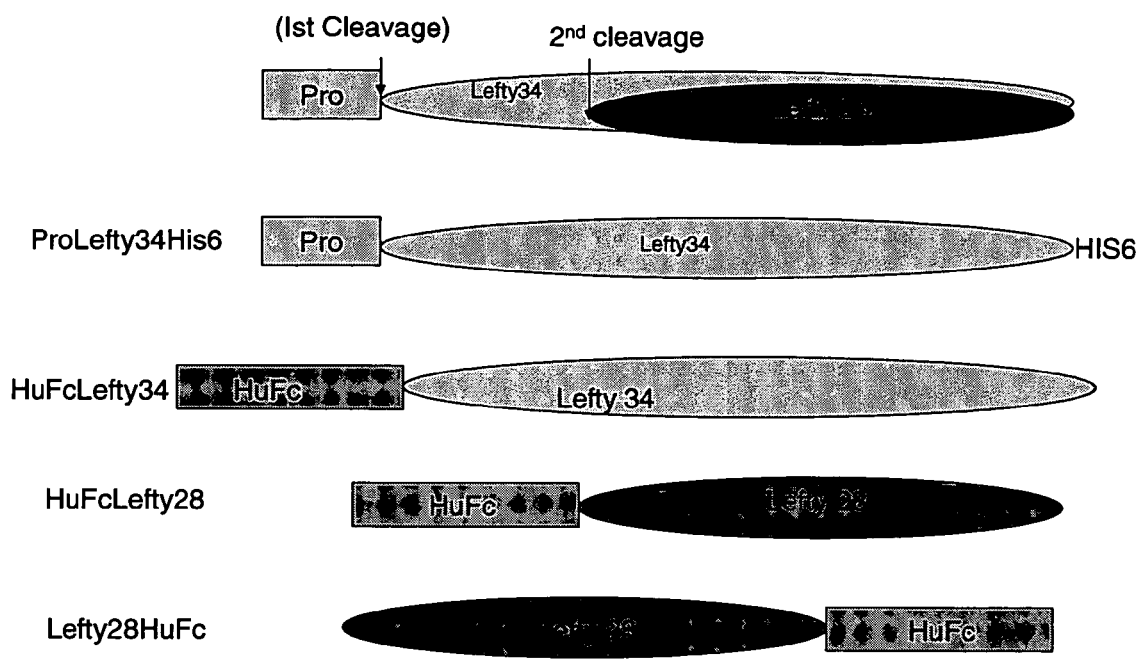
FIG. 6 is a schematic diagram showing various human Lefty A constructs that were prepared and tested for myostatin binding. The larger forms (34 kDa, or "Lefty 34") included an alteration to inactivate the second RXXR cleavage site. The natural signal sequence was replaced (along with two alanine residues C-terminal thereto) with a honey bee melatin leader sequence. The shorter forms (28 kDa, or "Lefty 28") contained the melatin leader sequence followed by an amino-terminally truncated Lefty sequence beginning with the Leucine that immediately follows the second RXXR cleavage sequence. N- and C-terminal Fc fusions were prepared as shown.

The various Lefty-A constructs described in FIG. 6 were subcloned into pAID4 vector and plasmid cDNAs were transfected (10 ug DNA) transiently into Cos cells by lipofectamine method. After six hours, growth media was added. Twenty four hours later, media was changed to serum free media and harvested after 48 hours. After centrifugation, supernatant was collected and kept at −20 C.

The constructs produced and tested replace the endogenous Lefty-A signal sequence with a honey melatin sequence. The following Lefty-A sequence was fused to the melatin for expression of the 34 kDa (long) form:

```
                                                  (SEQ ID NO:11)
LTEEQLLGSLLRQLQLSEVPVLDRADMEKLVIPAHVRAQYVVLLRRSHGD

RSRGKRFSQSFREVAGRFLASEASTHLLVFGMEQRLPPNSELVQAVLRLF

QEPVPKAALHGHRLSPRSAQARVTVEWLRVRDDGSNRTSLIDSRLVSVH

ESGWKAFDVTEAVNFWQQLSRPRQPLLLQVSVQREHLGPLASGAHKLVRF

ASQGAPAGLGEPQLELHTLDLRDYGAQGDCDPEAPMTEGTRCCRQEMYID

LQGMKWAKNWVLEPPGFLAYECVGTCQQPPEALAFNWPFLGPRQCIASET

ASLPMIVSIKEGGRTRPQVVSLPNMRVQKCSCASDGALVPRRLQP
```

The bold "F" indicates the expected first amino acid of the mature 34 kDa form. The underlined "G" shows the site of an R−>G alteration to eliminate the second RXXR cleavage site.

The following sequence was fused to the melatin leader for expression of the 28 kDa (short) form of Lefty-A:

(SEQ ID NO:12)
LSPRSAQARVTVEWLRVRDDGSNRTSLIDSRLVSVHESGWKAFDVTEAVN

FWQQLSRPRQPLLLQVSVQREHLGPLASGAHKLVRFASQGAPAGLGEPQL

ELHTLDLRDYGAQGDCDPEAPMTEGTRCCRQEMYIDLQGMKWAKNWVLEP

PGFLAYECVGTCQQPPEALAFNWPFLGPRQCIASETASLPMIVSIKEGGR

TRPQVVSLPNMRVQKCSCASDGALVPRRLQP

The various Fc fusions described in FIG. 6 were generated based on the above "Lefty 34" and "Lefty 28" constructs.

Example 2

Lefty-A Polypeptides Bind to Myostatin

Figure 7:
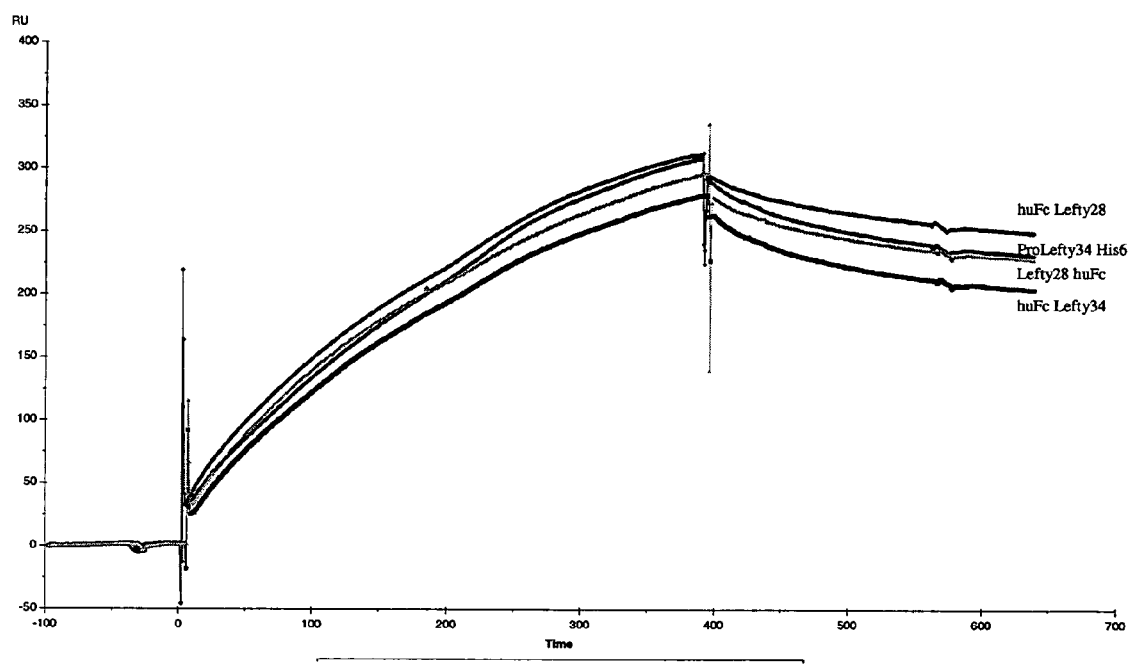
FIG. 7 shows data from a Biacore™ binding assay. GDF-11 was immobilized on a Biacore chip and conditioned medium from cells expressing the various Lefty constructs was passaged through the chip. The rising curve indicates protein binding, which decreases during the subsequent wash phase. Control samples show little or no binding. These data demonstrate that Lefty 34 and Lefty 28 bind directly to myostatin.

BiaCore chip analysis was carried out with each of the Lefty constructs. GDF-11 is a close homolog of myostatin that regulates neurological processes. GDF-11 was immobilized on a BiaCore CM5 chip using standard amine coupling procedure. As shown in FIG. 7, each of the Lefty constructs binds to myostatin.

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A recombinant Lefty derivative polypeptide comprising an amino acid sequence as set forth in the formula: W-A-X-B-Y,
   wherein A consists essentially of an amino acid sequence at least 85% identical to the sequence of Region 2 of SEQ ID NO: 1;
   wherein B consists essentially of an amino acid sequence at least 85% identical to the sequence of Region 4 of SEQ ID NO: 1;
   wherein X consists of zero, one or more than one amino acid;
   wherein W consists of zero, one or more than one amino acid;
   wherein Y consists of zero, one or more than one amino acid;
   wherein the recombinant Lefty derivative polypeptide binds to one or more of Nodal, myostatin and GDF-11;
   wherein the recombinant Lefty derivative polypeptide is not a wild-type Lefty polypeptide;
   wherein the recombinant Lefty derivative polypeptide comprises an amino acid sequence that is at least 95% identical to a human Lefty polypeptide sequence selected from the group consisting of amino acids 78-353 of SEQ ID NO: 1 and amino acids 78-353 of SEQ ID NO:2; and
   wherein the recombinant Lefty derivative polypeptide comprises one or more mutations within the RXXR cleavage sequence corresponding to amino acid residues 132-135 of SEQ ID NO: 1 or 2 so as to prevent cleavage at the mutated sequence.

2. The recombinant Lefty derivative polypeptide of claim 1, wherein the recombinant Lefty derivative polypeptide comprises an amino acid sequence that is at least 85% identical to the cysteine knot portion of a human Lefty polypeptide.

3. The recombinant Lefty derivative polypeptide of claim 1, wherein A consists of an amino acid sequence at least 95% identical to the sequence of Region 2 of SEQ ID NO: 1 and wherein B consists of an amino acid sequence at least 95% identical to the sequence of Region 4 of SEQ ID NO:1.

4. The recombinant Lefty derivative polypeptide of claim 1, wherein A is selected from the group consisting of: CRQEMYIDLQGMKWAKNWVLEPPG FLAYECVGT (SEQ ID NO: 5) and CRQEMYIDLQGMKWAENWVLEPPG-FLAYECVGT (SEQ ID NO: 7), and wherein B is selected from the group consisting of: CIASETASLPMIVSIKEGGR-TRPQVVSLPNMRVQKC (SEQ ID NO: 6) and CIASETD-SLPMIVSIKEGGRTRPQVVSLPNMRVQKC (SEQ ID NO: 8).

5. The recombinant Lefty derivative polypeptide of claim 1, wherein X comprises an amino acid sequence that has low immunogenicity.

6. The recombinant Lefty derivative polypeptide of claim 1, wherein X comprises a glycosylation site.

7. The recombinant Lefty derivative polypeptide of claim 1, wherein the length of X is between 0-50 amino acids.

8. The recombinant Lefty derivative polypeptide of claim 1, wherein X comprises a dimerization domain.

9. The recombinant Lefty derivative polypeptide of claim 1, wherein the polypeptide is fused to an additional domain.

10. The recombinant Lefty derivative polypeptide of claim 9, wherein the additional domain is a dimerization domain.

11. The recombinant Lefty derivative polypeptide of claim 9, wherein the additional domain is fused to the carboxyl or amino terminus of the Lefty polypeptide.

12. The recombinant Lefty derivative polypeptide of claim 10, wherein the dimerization domain comprises a Lefty propeptide sequence.

13. The recombinant Lefty derivative polypeptide of claim 11, wherein the dimerization domain is selected from an immunoglobulin heavy chain constant region and an immunoglobulin light chain constant region.

14. The recombinant Lefty derivative polypeptide of claim 10, wherein the dimerization domain is a leucine zipper domain.

15. The recombinant Lefty derivative polypeptide of claim 14, wherein said leucine zipper domain comprises at least four leucine heptads.

16. The recombinant Lefty derivative polypeptide of claim 15, wherein said leucine zipper domain is selected from the group consisting of a Fos and a Jun leucine zipper domain.

17. The recombinant Lefty derivative polypeptide of claim 10, further comprising a linker sequence interposed between and covalently joining the Lefty polypeptide and the dimerization domain.

18. The recombinant Lefty derivative polypeptide of claim 1, wherein X comprises a domain that binds Nodal, myostatin and/or GDF-11.

19. The recombinant Lefty derivative polypeptide of claim 9, wherein the additional domain is a domain that binds Nodal, myostatin and/or GDF-11.

20. The recombinant Lefty derivative polypeptide of claim 19, wherein the domain that binds Nodal, myostatin and/or GDF-11 inhibits the binding of Nodal, myostatin and/or GDF-11 to a Type I receptor.

21. The recombinant Lefty derivative polypeptide of claim 20 wherein the domain that binds Nodal, myostatin and/or GDF-11 competitively inhibits the binding of Nodal, myostatin and/or GDF-11 to a Type I receptor selected from the group consisting of ALK4 and ALK7.

22. The recombinant Lefty derivative polypeptide of claim 20, wherein the domain that binds Nodal, myostatin and/or GDF-11 is selected from the group consisting of:
    (a) an extracellular portion of ALK4;
    (b) an extracellular portion of ALK7;
    (c) an antigen-binding portion of an antibody that binds Nodal, myostatin and/or GDF-11; and
    (d) a randomized polypeptide that has been selected for binding to Nodal, myostatin and/or GDF-11.

23. The recombinant Lefty derivative polypeptide of claim 1, wherein said modified Lefty polypeptide inhibits signaling mediated by a protein selected from an ActRII receptor, myostatin, Nodal, and GDF-11 in a cell.

24. The recombinant Lefty derivative polypeptide of claim 1, wherein said modified Lefty polypeptide comprises a heterogenous sequence that mediates secretion of the recombinant Lefty derivative polypeptide.

25. The recombinant Lefty derivative polypeptide of claim 24, wherein said heterogenous sequence that mediates secretion of the recombinant Lefty derivative polypeptide is a honey bee melatin leader sequence.

26. An isolated Lefty polypeptide complex comprising:
    a) a first Lefty polypeptide; and
    b) a second Lefty polypeptide,
    wherein the first and second Lefty polypeptides are associated to form a complex, wherein the complex binds to a TGF-β family member selected from the group consisting of: myostatin, Nodal and GDF-11, and wherein at least one of the Lefty polypeptides of the complex comprises one or more mutations within the RXXR cleavage sequence corresponding to amino acid residues 132-135 of SEQ ID NO:1 or 2 so as to prevent cleavage at the mutated sequence.

27. The Lefty polypeptide complex of claim 26, wherein the polypeptide complex is a homodimer.

28. A pharmaceutical preparation comprising a modified Lefty polypeptide of claim 1.

29. A recombinant Lefty derivative polypeptide comprising an amino acid sequence as set forth in the formula: W-A-X-B-Y;
    wherein the Lefty derivative polypeptide comprises an amino acid sequence that is at least 85% identical to a human Lefty polypeptide sequence selected from the group consisting of: SEQ ID NO:1 and SEQ ID NO:2;
    wherein A is selected from the group consisting of: CRQE-MYIDLQGMKWAKNWVLEPPGFLAYECVGT (SEQ ID NO: 5) and CRQEMYIDLQGMKWAENWV-LEPPGFLAYECVGT (SEQ ID NO: 7);
    wherein B is selected from the group consisting of: CIASETASLPMIVSIKEGGRTRPQVVS-LPNMRVQKC (SEQ ID NO: 6) and CIASETDSLP-MIVSIKEGGRTRPQVVSLPNMRVQKC (SEQ ID NO: 8);
    wherein X consists of zero, one or more than one amino acid;
    wherein W consists of zero, one or more than one amino acid;
    wherein Y consists of zero, one or more than one amino acid;
    wherein the recombinant, Lefty derivative polypeptide binds to one or more of Nodal, myostatin and GDF-11;
    wherein the recombinant Lefty derivative polypeptide is not a wild-type Lefty polypeptide; and
    wherein the recombinant Lefty derivative polypeptide comprises one or more mutations within the RXXR cleavage sequence corresponding to amino acid residues 132-135 of SEQ ID NO: 1 or 2 so as to prevent cleavage at the mutated sequence.

30. The recombinant Lefty derivative polypeptide of claim 29, wherein the recombinant Lefty derivative polypeptide comprises an amino acid sequence that is at least 85% identical to SEQ ID NO: 1, and wherein A is SEQ ID NO: 5 and B is SEQ ID NO: 6.

31. The recombinant Lefty derivative polypeptide of claim 29, wherein the recombinant Lefty derivative polypeptide comprises an amino acid sequence that is at least 85% iden tical to SEQ ID NO: 2, and wherein A is SEQ ID NO: 7 and B is SEQ ID NO: 8.

32. The recombinant Lefty derivative polypeptide of claim 4, wherein the recombinant Lefty derivative polypeptide comprises an amino acid that is at least 95% identical to amino acids 78-353 of SEQ ID NO: 1, and wherein A is SEQ ID NO: 5 and B is SEQ ID NO: 6.

33. The recombinant Lefty derivative polypeptide of claim 29, wherein the recombinant Lefty derivative polypeptide comprises an amino acid that is at least 95% identical to amino acids 78-353 of SEQ ID NO: 2, and wherein A is SEQ ID NO: 7 and B is SEQ ID NO: 8.

* * * * *

UNITED STATES PATENT AND TRADEMARK OFFICE
CERTIFICATE OF CORRECTION

| | | |
|---|---|---|
| PATENT NO. | : 7,612,040 B2 | Page 1 of 1 |
| APPLICATION NO. | : 11/479181 | |
| DATED | : November 3, 2009 | |
| INVENTOR(S) | : Knopf et al. | |

It is certified that error appears in the above-identified patent and that said Letters Patent is hereby corrected as shown below:

On title page
(*) Notice: subject to any disclaimer, the term of this patent is extended or adjusted under 35 U.S.C. 154(b) by 33 days
Delete the phrase "33 days" and insert --159 days--;

Column 73, lines 26-27, please replace "Claim 11" with --Claim 10--;

Column 75, lines 3-4, please replace "Claim 4" with --Claim 29--.

Signed and Sealed this

Fifteenth Day of June, 2010

David J. Kappos
*Director of the United States Patent and Trademark Office*